(12) United States Patent
Gonzaga-Jauregui et al.

(10) Patent No.: US 11,098,363 B2
(45) Date of Patent: Aug. 24, 2021

(54) CORNULIN (CRNN) VARIANTS AND USES THEREOF

(71) Applicant: Regeneron Pharmaceuticals, Inc., Tarrytown, NY (US)

(72) Inventors: Claudia Gonzaga-Jauregui, Tarrytown, NY (US); Kavita Praveen, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/161,331

(22) Filed: Oct. 16, 2018

(65) Prior Publication Data

US 2019/0112663 A1 Apr. 18, 2019

Related U.S. Application Data

(60) Provisional application No. 62/572,958, filed on Oct. 16, 2017.

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS 6,312,922 B1 * 11/2001 Edwards .............. C07K 14/705
435/69.1
6,399,364 B1 * 6/2002 Reeve .................. C12Q 1/6874
435/287.1

FOREIGN PATENT DOCUMENTS

CN 106620694 10/2017

OTHER PUBLICATIONS

NCBI Database Gen Bank Accession No. AL703280.1, Sep. 4, 2003, available via URL: <ncbi.nlm.nih.gov/nuccore/AL703280.1/> (Year: 2003).*
Lieden et al. Allergy, Feb. 2009. vol 64, No. 2, p. 304-311 (Year: 2009).*
Salahshourifar et al Clin Oral Invest. 2015. 19: 2273-2283 (Year: 2015).*
Trzeciak et al International Archives of Allergy and Immunology. Apr. 2017. 172.1: 11-19 (Year: 2017).*
Taylan et al J Allergy Clin Immunol. 2015. 136(2):507-509 and Tables E1-E2, 22 pages (Year: 2015).*
Margolis et al., "Exome Sequencing of Filaggrin and Related Genes in African-American Children with Atopic Dermatitis", Journal of Investigative Dermatology, 2014, 134(8), pp. 2272-2274.
Salafishourifar et al., "Downregualtion of CRNN gene and genomic instability at 1q21.3 in oral squamous cell carcinoma", Clinical Oral Investigations, 2015, 19(9), pp. 2273-2283.
Sullivan et al., "Current and emerging concepts in atopic dermatitis pathogenesis", Clinics in Dermatology, 2017, 35 (4), pp. 349-353.
Taylan et al., "Whole-exome sequencing of Ethiopian patients with ichthyosis vulgaris and atopic dermatitis", The Journal of Allergy and Clinical Immunology, 2015, 136(2), pp. 507-509.

* cited by examiner

*Primary Examiner* — Carla J Myers
(74) *Attorney, Agent, or Firm* — Stradley Ronon Stevens & Young, LLP

(57) ABSTRACT

The disclosure provides nucleic acid molecules, including cDNA, comprising an alteration that encodes a loss-of-function cornulin (CRNN) protein. The disclosure also provides isolated and recombinant human loss-of-function cornulin protein variants that comprise a truncation at a position corresponding to position 79. The truncation, and the nucleic acid molecules encoding this change, associate with skin disorders such as, for example, psoriasis, eczema, or atopic dermatitis. The disclosure also provides methods for determining whether a subject has or has a risk of developing a skin disorder, based on the identification of such alterations in the nucleic acid molecules encoding CRNN. Subjects at risk for or who have a skin disorder may be treated with an agent effective to treat the skin disorder.

14 Claims, 3 Drawing Sheets

Specification includes a Sequence Listing.

US 11,098,363 B2

CORNULIN (CRNN) VARIANTS AND USES THEREOF

REFERENCE TO A SEQUENCE LISTING

This application includes a Sequence Listing submitted electronically as a text file named 18923800401SEQ, created on Oct. 14, 2018, with a size of 24 kilobytes. The Sequence Listing is incorporated by reference herein.

FIELD

The disclosure relates generally to the field of genetics. More particularly, the disclosure relates to gene alterations and polypeptide variants in Cornulin (CRNN) that associate with, for example, skin disorders.

BACKGROUND

Autoimmune disorders can affect a variety of organs with different degrees of severity. Certain autoimmune disorders can manifest with skin presentations where there is inflammation and others abnormalities can cause substantial physical and psychological distress in patients suffering from these immune-related skin disorders, such as psoriasis, eczema, or atopic dermatitis. Psoriasis is an immune related disorder that has primarily dermatological manifestations but can also affect the joints and some mucosal areas of the body. Patients suffering from the disease complain of inflammation, pain, and itching in addition to the appearance of dry patches of skin, named scales, or other lesions such as pustules and papules. Occurrence of skin disorders, such as psoriasis, in families is well-documented and therefore it is inferred that genetics play a significant role in the susceptibility to developing these diseases. However, beyond the major histocompatibility complex, few genes have been identified as significant contributors for the development of disease or conferring susceptibility to disease presentation.

SUMMARY

The present disclosure provides cDNA molecules comprising a nucleic acid sequence encoding a loss-of-function cornulin protein. In some embodiments, the loss-of-function cornulin protein comprises cysteine at the position corresponding to position 69 according to SEQ ID NO:8. In some embodiments, the loss-of-function cornulin protein comprises cysteine at the position corresponding to position 69 according to SEQ ID NO:8, and is truncated at a position corresponding to position 79 according to SEQ ID NO:8. In some embodiments, the loss-of-function cornulin protein comprises a different amino acid compared to the wild type cornulin protein at any one of the positions corresponding to positions 69 to 76, 78, and 79 according to SEQ ID NO:8. In some embodiments, the loss-of-function cornulin protein comprises the amino acid sequence of SEQ ID NO:10 at the positions corresponding to positions 69 to 79 according to SEQ ID NO:8. In some embodiments, the loss-of-function cornulin protein comprises the amino acid sequence according to SEQ ID NO:8, or an amino acid sequence that has at least 90% sequence identity to SEQ ID NO:8 and comprises a cysteine at a position corresponding to position 69 according to SEQ ID NO:8. In some embodiments, the loss-of-function cornulin protein comprises the amino acid sequence according to SEQ ID NO:10. In some embodiments, the cDNA comprises a thymine at a position corresponding to position 205 according to SEQ ID NO:6. In some embodiments, the cDNA comprises the codons ACT and TGT at positions corresponding to positions 202 to 204 and 205 to 207, respectively, according to SEQ ID NO:6. In some embodiments, the cDNA comprises SEQ ID NO:6.

The present disclosure also provides vectors comprising any of the cDNA molecule described herein.

The present disclosure also provides host cells comprising any of the cDNA molecules described herein. In some embodiments, the host cells comprises any of the vectors described herein. In some embodiments, the cDNA is operably linked to a promoter active in the host cell. In some embodiments, the host cell is a mammalian cell.

The present disclosure also provides alteration-specific probes or primers comprising a nucleic acid sequence which is complementary to a nucleic acid sequence of a nucleic acid molecule encoding a loss-of-function cornulin protein truncated at a position corresponding to position 79 according to SEQ ID NO:8, wherein the alteration-specific probe or primer comprises a nucleic acid sequence which is complementary to a portion of the nucleic acid molecule encompassing the codon which encodes a cysteine at the position corresponding to the position 69 according to SEQ ID NO:8. In some embodiments, the alteration-specific probe or primer comprises at least about 15 nucleotides. In some embodiments, the alteration-specific probes or primers comprise a label. In some embodiments, the label is a fluorescent label, a radiolabel, or biotin.

The present disclosure also provides methods for diagnosing a skin disorder or detecting a risk of developing a skin disorder in a human subject, comprising: detecting a nucleic acid molecule encoding a loss-of-function cornulin protein obtained from the human subject; and/or detecting a loss-of-function cornulin protein obtained from the human subject; and diagnosing the human subject with the skin disorder if the subject has one or more symptoms of the skin disorder, or diagnosing the human subject as at risk for developing a skin disorder if the subject does not have one or more symptoms of the skin disorder. In some embodiments, the skin disorder is psoriasis, eczema, or atopic dermatitis.

BRIEF DESCRIPTION OF THE FIGURES

The accompanying figures, which are incorporated in and constitute a part of this specification, illustrate several aspects and together with the description serve to explain the principles of the present disclosure.

Figure 1:
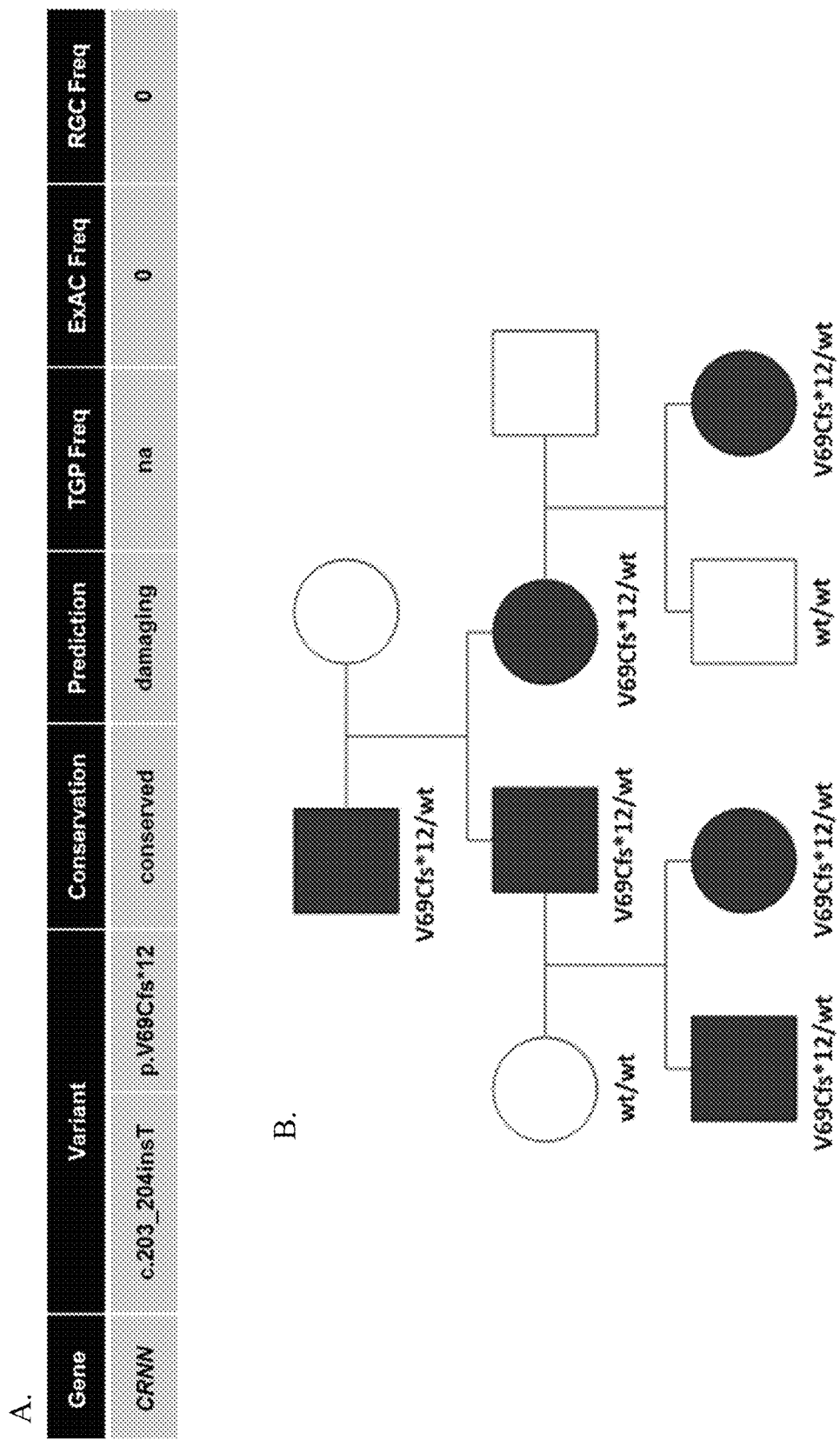
FIG. 1 (Panels A, B, C, and D) shows identification and segregation of an insertion novel rare variant in the CRNN gene that produces a frameshift and a downstream truncation of the CRNN protein at position 79 in a family with the skin disorder diagnosed as psoriasis. Panel D shows sequences SEQ ID NO:11, SEQ ID NO:12, SEQ ID NO:13, SEQ ID NO:14, SEQ ID NO:15, SEQ ID NO:16, SEQ ID NO:17, and SEQ ID NO:18, top to bottom.
Figure 1:
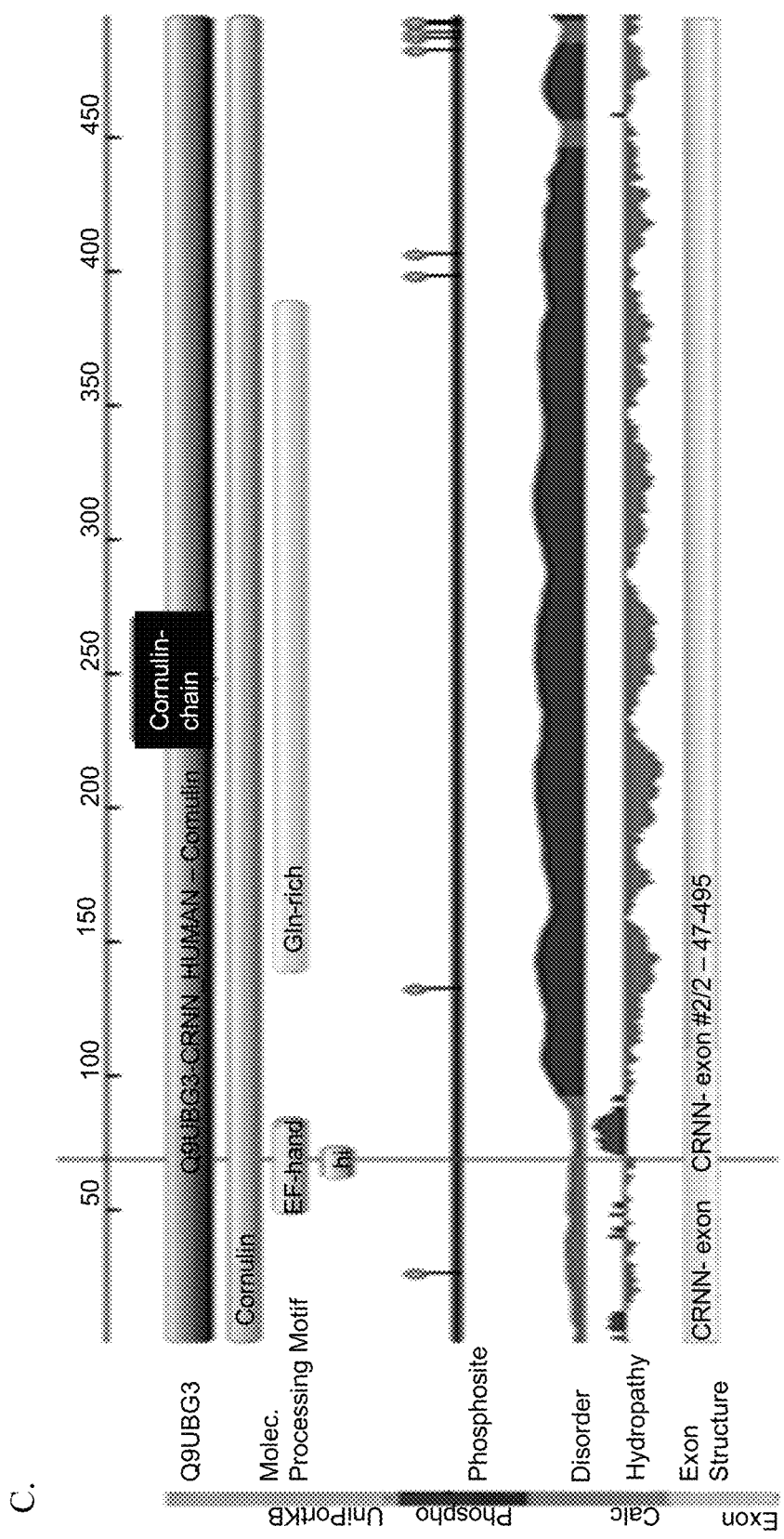
Figure 1:
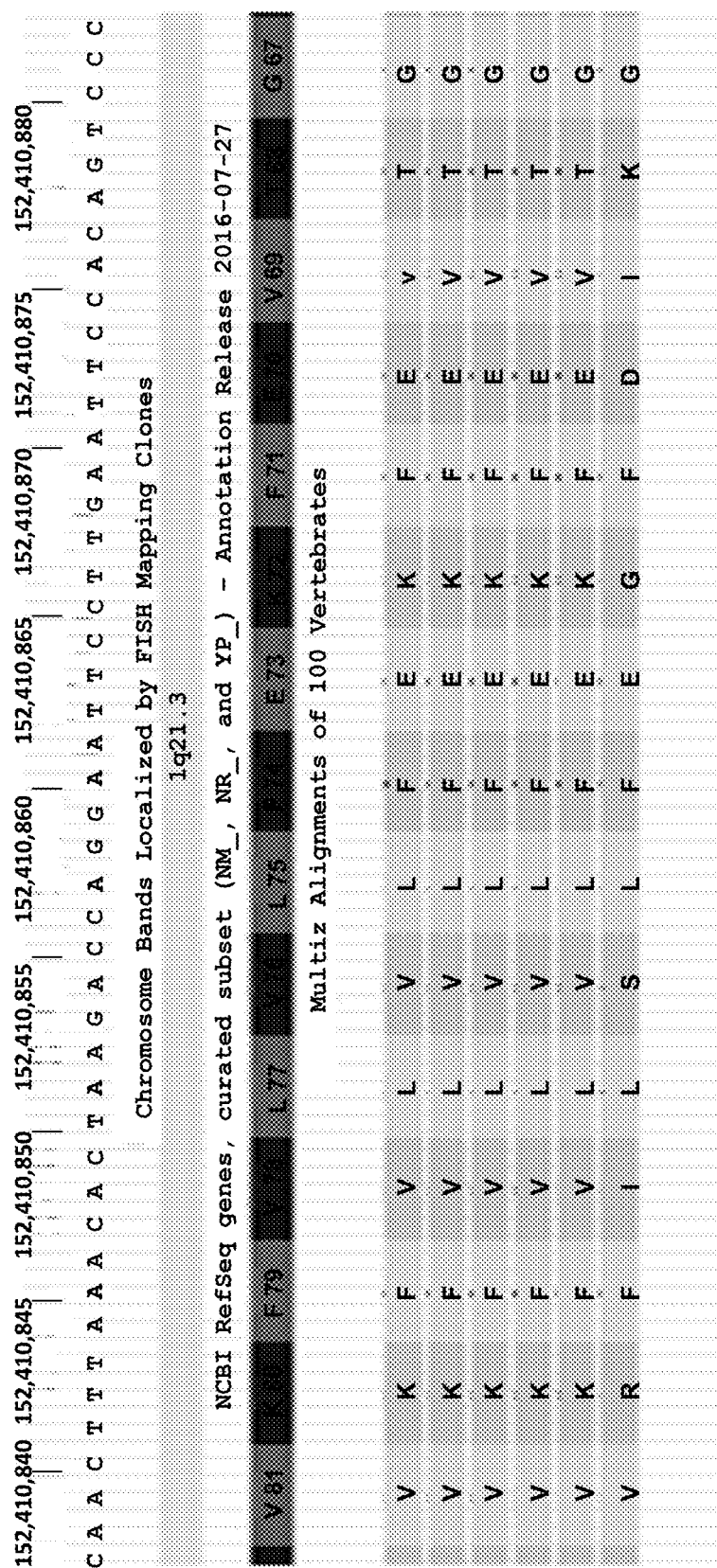

Additional advantages of the present disclosure will be set forth in part in the description which follows, and in part will be apparent from the description, or can be learned by practice of the embodiments disclosed herein. The advantages of the present disclosure will be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION

The study of rare variants in families with skin disorders, such as psoriasis, eczema, or atopic dermatitis, provides a major opportunity to uncover novel genes that play a role in disease development, including those involved in immune regulation or epidermal differentiation, integrity and maintenance that may render the carrier individuals more susceptible to environmental insults that can trigger disease presentation. The present disclosure provides CRNN variants that will aid in understanding the biology of CRNN, and will facilitate the diagnosis and treatment of subjects with skin disorders.

Various references, including patents, patent applications, accession numbers, technical articles, and scholarly articles are cited throughout the specification. Each reference is incorporated by reference herein, in its entirety and for all purposes.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, without limitation, farm animals (e.g., horse, cow, pig), companion animals (e.g., dog, cat), laboratory animals (e.g., mouse, rat, rabbits), and non-human primates. In some embodiments, the subject is a human.

As used herein, a "nucleic acid," a "nucleic acid molecule," a "nucleic acid sequence," "polynucleotide," or "oligonucleotide" can comprise a polymeric form of nucleotides of any length, may comprise DNA and/or RNA, and can be single-stranded, double-stranded, or multiple stranded. One strand of a nucleic acid also refers to its complement.

As used herein, the phrase "corresponding to" or grammatical variations thereof when used in the context of the numbering of a given amino acid or nucleic acid sequence or position refers to the numbering of a specified reference sequence when the given amino acid or nucleic acid sequence is compared to the reference sequence (e.g., with the reference sequence herein being the nucleic acid molecule or polypeptide of (wild type or full length) CRNN). In other words, the residue (e.g., amino acid or nucleotide) number or residue (e.g., amino acid or nucleotide) position of a given polymer is designated with respect to the reference sequence rather than by the actual numerical position of the residue within the given amino acid or nucleic acid sequence. For example, a given amino acid sequence can be aligned to a reference sequence by introducing gaps to optimize residue matches between the two sequences. In these cases, although the gaps are present, the numbering of the residue in the given amino acid or nucleic acid sequence is made with respect to the reference sequence to which it has been aligned.

For example, the phrase "CRNN protein truncated at a position corresponding to position 79 according to SEQ ID NO:8" (and similar phrases) means that, if the amino acid sequence of the CRNN protein is aligned to the sequence of SEQ ID NO:8, the CRNN protein truncates at the position that corresponds to position 79 of SEQ ID NO:8 (e.g., the terminal amino acid of the CRNN protein is the amino acid at position 79). Or, in other words, these phrases refer to a CRNN protein which has a truncation at a position that is homologous to position 79 of SEQ ID NO:8. Herein, such a protein is also referred to as "a truncated CRNN protein." "A variant CRNN protein" includes both truncated CRNN proteins and loss-of-function CRNN proteins.

A CRNN protein truncated at a position corresponding to position 79 according to SEQ ID NO:8 can easily be identified by performing a sequence alignment between the given CRNN protein and the amino acid sequence of SEQ ID NO:8. Likewise, a CRNN protein having a cysteine at a position corresponding to position 69 according to SEQ ID NO:8 can easily be identified by performing a sequence alignment between the given CRNN protein and the amino acid sequence of SEQ ID NO:8. A variety of computational algorithms exist that can be used for performing a sequence alignment in order to identify a truncation at a position that corresponds to position 79 in SEQ ID NO:8, or to identify a cysteine at a position that corresponds to position 69 according to SEQ ID NO:8. For example, by using the NCBI BLAST algorithm (Altschul et al., 1997, Nucleic Acids Res., 25, 3389-3402) or CLUSTALW software (Sievers et al., 2014, Methods Mol. Biol., 1079, 105-116) sequence alignments may be performed. However, sequences can also be aligned manually.

It has been observed in accordance with the disclosure that certain variations in CRNN associate with a risk of developing a skin disorder. It is believed that no variants of the CRNN gene or protein have any known association with skin disorders in humans. A rare variant in the CRNN gene segregating with the phenotype of a skin disorder in affected family members has been identified in accordance with the present disclosure. For example, a genetic alteration that results in an insertion of a thymine at position 205 of the human CRNN mRNA or cDNA (e.g., SEQ ID NO:4 and SEQ ID NO:6, respectively), which results in a frameshift producing a CRNN protein that is truncated at a position corresponding to position 79 according to SEQ ID NO:8 (e.g., the terminal amino acid is located at position 79), has been observed to indicate that the human having such an alteration may develop a skin disorder, such as psoriasis. Altogether, the genetic analyses described herein suggest that the CRNN gene and, in particular, truncating or loss-of-function variants in the CRNN gene, associate with increased susceptibility to develop a skin disorder, such as psoriasis. Therefore, human subjects having CRNN alterations that associate with a skin disorder may be treated such that the skin disorder is inhibited, the symptoms thereof are reduced, and/or development of symptoms is repressed. Accordingly, the present disclosure provides isolated or recombinant CRNN variant genes, including cDNA and mRNA, as well as isolated or recombinant CRNN variant polypeptides. Additionally, the disclosure provides methods for leveraging the identification of such variants in subjects to identify or stratify risk in such subjects of developing a skin disorder, or to diagnose subjects as having a skin disorder, such that subjects at risk or subjects with active disease may be treated.

The amino acid sequence for wild type CRNN protein is set forth in SEQ ID NO:7. The wild type CRNN protein having SEQ ID NO:7 is 495 amino acids in length. Referring to SEQ ID NO:7, positions 69 to 79 of the wild type CRNN protein comprise the following amino acids in the recited order: Val-Glu-Phe-Lys-Glu-Phe-Leu-Val-Leu-Val-Phe (SEQ ID NO:9).

The present disclosure provides nucleic acid molecules (i.e., genomic DNA, mRNA, and cDNA) encoding CRNN variant polypeptides, and CRNN variant polypeptides, that have been demonstrated herein to be associated with skin disorders such as, for example, psoriasis, eczema, and atopic dermatitis.

The present disclosure provides isolated nucleic acid molecules comprising a nucleic acid sequence encoding a human CRNN protein, wherein the protein is a loss-of-function CRNN protein or a CRNN protein truncated at a position corresponding to position 79 according to SEQ ID NO:8, or the complement of the nucleic acid sequence.

The present disclosure also provides genomic DNA molecules comprising a nucleic acid sequence encoding at least a portion of a human CRNN protein, wherein the protein is a loss-of-function CRNN protein or a CRNN protein truncated at a position corresponding to position 79 according to SEQ ID NO:8, or the complement of the nucleic acid sequence.

The present disclosure provides nucleic acid molecules encoding CRNN variant proteins that associate with skin disorders. In some embodiments, the nucleic acid molecules encode a loss-of-function CRNN protein. In some embodiments, the nucleic acid molecules encode a truncated CRNN protein. For example, the present disclosure provides isolated nucleic acid molecules comprising a nucleic acid sequence encoding a human CRNN protein, wherein the protein is truncated at a position corresponding to position 79 according to SEQ ID NO:8, or the complement of the nucleic acid sequence.

In some embodiments, the isolated nucleic acid molecule comprises or consists of a nucleic acid sequence that encodes a truncated CRNN protein comprising a cysteine at a position corresponding to position 69 according to SEQ ID NO:8.

In some embodiments, the isolated nucleic acid molecule comprises or consists of a nucleic acid sequence that encodes a truncated CRNN protein comprising the amino acid sequence of SEQ ID NO:10 at the positions corresponding to positions 69 to 79 according to SEQ ID NO:8.

In some embodiments, the nucleic acid molecule comprises or consists of a nucleic acid sequence that encodes a human CRNN protein having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8, or the complement of the nucleic acid sequence. Herein, if reference is made to percent sequence identity, the higher percentages of sequence identity are preferred over the lower ones.

In some embodiments, the isolated nucleic acid molecule comprises or consists of a nucleic acid sequence that encodes a truncated CRNN protein, wherein the truncated CRNN protein comprises the amino acid sequence of SEQ ID NO:8, or an amino acid sequence that has at least 90% sequence identity to SEQ ID NO:8 and comprises a cysteine at a position corresponding to position 69 according to SEQ ID NO:8.

The nucleic acid sequence of wild type CRNN genomic DNA is set forth in SEQ ID NO:1. The wild type CRNN genomic DNA comprising SEQ ID NO:1 is 5,009 nucleotides in length. Referring to SEQ ID NO:1, position 3375 of the wild type CRNN genomic DNA is a guanine.

The present disclosure provides genomic DNA molecules encoding a variant CRNN protein. In some embodiments, the genomic DNA molecules encode a loss-of-function CRNN protein. In some embodiments, the genomic DNA molecules encode a truncated CRNN protein. In some embodiments, the genomic DNA comprises or consists of a nucleic acid sequence encoding a CRNN protein truncated at a position corresponding to position 79 according to SEQ ID NO:8. In some embodiments, the genomic DNA comprises or consists of a nucleic acid sequence encoding a CRNN protein truncated at a position corresponding to position 79 according to SEQ ID NO:8, and that comprises a cysteine at a position corresponding to position 69 according to SEQ ID NO:8. In some embodiments, the genomic DNA comprises or consists of a nucleic acid sequence encoding a CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the genomic DNA comprises or consists of a nucleic acid sequence that encodes a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the genomic DNA comprises or consists of a nucleic acid sequence encoding a variant CRNN protein having SEQ ID NO:8. In some embodiments, the genomic DNA comprises or consists of a nucleic acid sequence that encodes a truncated CRNN protein, wherein the truncated CRNN protein comprises the amino acid sequence of SEQ ID NO:8, or an amino acid sequence that has at least 90% sequence identity to SEQ ID NO:8 and comprises a cysteine at a position corresponding to position 69 according to SEQ ID NO:8.

In some embodiments, the genomic DNA comprises or consists of a nucleic acid sequence comprising a thymine at a position corresponding to position 3375 according to SEQ ID NO:2. In contrast, the wild type CRNN genomic DNA comprises a guanine at a position corresponding to position 3375 according to SEQ ID NO:1. The insertion of this thymine into the variant CRNN genomic DNA produces a one nucleotide base frameshift, thereby resulting in a truncated CRNN protein having a cysteine at a position corresponding to position 69 according to SEQ ID NO:8. In some embodiments, the genomic DNA comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a thymine at a position corresponding to position 3375 according to SEQ ID NO:2. In some embodiments, the genomic DNA comprises or consists of a nucleic acid sequence according to SEQ ID NO:2.

In some embodiments, the isolated nucleic acid molecules comprise less than the entire genomic DNA sequence. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 contiguous nucleotides of SEQ ID NO:2. In some embodiments, the isolated nucleic acid molecules comprise or consist of at least about 1000 to at least about 2000 contiguous nucleotides of SEQ ID NO:2.

In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:2. In some embodiments, such contiguous nucleotides may be combined with other nucleic acid molecules of contiguous nucleotides to produce the cDNA molecules described herein.

Such isolated nucleic acid molecules can be used, for example, to express variant CRNN mRNAs and proteins or as exogenous donor sequences. It is understood that gene sequences within a population can vary due to polymorphisms, such as SNPs. The examples provided herein are only exemplary sequences, and other sequences are also possible.

In some embodiments, the isolated nucleic acid molecules comprise a variant CRNN minigene, in which one or more nonessential segments encoding SEQ ID NO:8 have been deleted with respect to a corresponding wild type CRNN genomic DNA. In some embodiments, the deleted nonessential segment(s) comprise one or more intron sequences. In some embodiments, the CRNN minigene has at least about 70%, at least about 75%, at least about 80%, at least about 85%, at least about 90%, at least about 95%, at least about 96%, at least about 97%, at least about 98%, at least about 99%, or 100% sequence identity to a portion of SEQ ID NO:2, wherein the minigene comprises a nucleic acid sequence having a thymine at a position corresponding to position 3375 according to SEQ ID NO:2.

The nucleic acid sequence of wild type CRNN mRNA is set forth in SEQ ID NO:3. The wild type CRNN mRNA comprising SEQ ID NO:3 is 1485 nucleotides in length. Referring to SEQ ID NO:3, position 205 of the wild type CRNN mRNA is a guanine.

The present disclosure also provides mRNA molecules comprising a nucleic acid sequence encoding at least a portion of a human CRNN protein, wherein the protein is a loss-of-function CRNN protein or a CRNN protein truncated at a position corresponding to position 79 according to SEQ ID NO:8, or the complement of the nucleic acid sequence.

The present disclosure also provides mRNA molecules encoding a variant CRNN protein. In some embodiments, the mRNA molecules encode a loss-of-function CRNN protein. In some embodiments, the mRNA molecules encode a truncated CRNN protein. In some embodiments, the mRNA comprises or consists of a nucleic acid sequence encoding a CRNN protein truncated at a position corresponding to position 79 according to SEQ ID NO:8. In some embodiments, the mRNA comprises or consists of a nucleic acid sequence encoding a CRNN protein truncated at a position corresponding to position 79 according to SEQ ID NO:8, and that comprises a cysteine at a position corresponding to position 69 according to SEQ ID NO:8. In some embodiments, the mRNA comprises or consists of a nucleic acid sequence encoding a CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the mRNA comprises or consists of a nucleic acid sequence that encodes a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the mRNA comprises or consists of a nucleic acid sequence encoding a variant CRNN protein having SEQ ID NO:8. In some embodiments, the mRNA comprises or consists of a nucleic acid sequence that encodes a truncated CRNN protein, wherein the truncated CRNN protein comprises the amino acid sequence of SEQ ID NO:8, or an amino acid sequence that has at least 90% sequence identity to SEQ ID NO:8 and comprises a cysteine at a position corresponding to position 69 according to SEQ ID NO:8.

In some embodiments, the mRNA comprises or consists of a nucleic acid sequence comprising a uracil at a position corresponding to position 205 according to SEQ ID NO:4. In contrast, the wild type CRNN mRNA comprises a guanine at a position corresponding to position 205 according to SEQ ID NO:3. The insertion of this uracil into the variant CRNN mRNA produces a one nucleotide base frameshift, thereby resulting in a truncated CRNN protein having a cysteine at a position corresponding to position 69 according to SEQ ID NO:8. In some embodiments, the mRNA comprises or consists of a nucleic acid sequence comprising the codons ACU and UGU at positions corresponding to positions 202 to 204 and 205 to 207, respectively, according to SEQ ID NO:4. In contrast, the wild type CRNN mRNA comprises the codons ACU and GUG at positions corresponding to positions 202 to 204 and 205 to 207, respectively, according to SEQ ID NO:3. In some embodiments, the mRNA comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises a uracil at a position corresponding to position 205 according to SEQ ID NO:4. In some embodiments, the mRNA comprises or consists of a nucleic acid sequence according to SEQ ID NO:4.

In some embodiments, the isolated nucleic acid molecule comprises less nucleotides than the entire CRNN mRNA sequence. In some embodiments, the isolated nucleic acid molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, or at least about 200 contiguous nucleotides of SEQ ID NO:4. In some embodiments, the isolated nucleic acid molecules comprise or consist of at least about 100 to at least about 200 contiguous nucleotides of SEQ ID NO:4. In this regard, the longer mRNA molecules are preferred over the shorter ones. In some embodiments, the isolated nucleic acid molecules comprise or consist of at least about 50, at least about 60, at least about 70, at least about 80, at least about 90, at least about 100, or at least about 200 contiguous nucleotides of SEQ ID NO:4. In this regard, the longer mRNA molecules are preferred over the shorter ones. In some embodiments, such mRNA molecules include the codon that encodes the cysteine at the position that corresponds to position 69 according to SEQ ID NO:8. In some embodiments, such mRNA molecules include the uracil at the position corresponding to position 205 according to SEQ ID NO:4. In some embodiments, such mRNA molecules include the codons ACU and UGU at positions corresponding to positions 202 to 204 and 205 to 207, respectively, according to SEQ ID NO:4.

The nucleic acid sequence of wild type CRNN cDNA is set forth in SEQ ID NO:5. The wild type CRNN cDNA comprising SEQ ID NO:5 is 1485 nucleotides in length, excluding the stop codon. Referring to SEQ ID NO:5, position 205 of the wild type CRNN cDNA is a guanine.

The present disclosure also provides cDNA molecules comprising a nucleic acid sequence encoding at least a portion of a human CRNN protein, wherein the protein is a loss-of-function CRNN protein or a CRNN protein truncated at a position corresponding to position 79 according to SEQ ID NO:8, or the complement of the nucleic acid sequence.

The present disclosure also provides cDNA molecules encoding a variant CRNN protein. In some embodiments, the cDNA molecules encode a loss-of-function CRNN protein. In some embodiments, the cDNA molecules encode a truncated CRNN protein. In some embodiments, the cDNA comprises or consists of a nucleic acid sequence encoding a CRNN protein truncated at a position corresponding to position 79 according to SEQ ID NO:8. In some embodiments, the cDNA comprises or consists of a nucleic acid sequence encoding a CRNN protein truncated at a position corresponding to position 79 according to SEQ ID NO:8, and that comprises a cysteine at a position corresponding to position 69 according to SEQ ID NO:8. In some embodiments, the cDNA comprises or consists of a nucleic acid sequence encoding a CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the cDNA comprises or consists of a nucleic acid sequence that encodes a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the cDNA comprises or consists of a nucleic acid sequence encoding a variant CRNN protein having SEQ ID NO:8. In some embodiments, the cDNA comprises or consists of a nucleic acid sequence that encodes a truncated CRNN protein, wherein the truncated CRNN protein comprises the amino acid sequence of SEQ ID NO:8, or an amino acid sequence that has at least 90% sequence identity to SEQ ID NO:8, and comprises a cysteine at a position corresponding to position 79 according to SEQ ID NO:8.

In some embodiments, the cDNA comprises or consists of a nucleic acid sequence comprising a thymine at a position corresponding to position 205 according to SEQ ID NO:6. In contrast, the wild type CRNN cDNA comprises a guanine at a position corresponding to position 205 according to SEQ ID NO:5. The insertion of this thymine into the variant CRNN mRNA produces a one nucleotide base frameshift, thereby resulting in a truncated CRNN protein having a cysteine at a position corresponding to position 69 according to SEQ ID NO:8. In some embodiments, the cDNA comprises or consists of a nucleic acid sequence comprising the codons ACT and TGT at positions corresponding to positions 202 to 204 and 205 to 207, respectively, according to SEQ ID NO:6. In contrast, the wild type CRNN cDNA comprises the codons ACT and GTG at positions corresponding to positions 202 to 204 and 205 to 207, respectively, according to SEQ ID NO:5. In some embodiments, the cDNA comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises a thymine at a position corresponding to position 205 according to SEQ ID NO:6. In some embodiments, the cDNA comprises or consists of a nucleic acid sequence according to SEQ ID NO:6.

In some embodiments, the cDNA molecules comprise less than the entire sequence of the variant CRNN cDNA molecule. In some embodiments, the cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, or at least about 200 contiguous nucleotides of SEQ ID NO:6. In some embodiments, the cDNA molecule comprises or consists of at least about 100 to at least about 200 contiguous nucleotides of SEQ ID NO:6. In this regard, the longer cDNA molecules are preferred over the shorter ones. In some embodiments, the cDNA molecules comprise or consist of at least about 50, at least about 60, at least about 70, at least about 80, at least about 90, at least about 100, or at least about 200 contiguous nucleotides of SEQ ID NO:6. In this regard, the longer cDNA molecules are preferred over the shorter ones. In some embodiments, such cDNA molecules include the codon that encodes the cysteine at the position that corresponds to position 69 according to SEQ ID NO:8. In some embodiments, such cDNA molecules include the thymine at the position corresponding to position 205 according to SEQ ID NO:6. In some embodiments, such cDNA molecules include the codons ACT and TGT at positions corresponding to positions 202 to 204 and 205 to 207, respectively, according to SEQ ID NO:6.

The present disclosure also provides isolated nucleic acid molecules that hybridize to variant CRNN genomic DNA (such as SEQ ID NO:2), variant CRNN minigenes, variant CRNN mRNA (such as SEQ ID NO:4), and/or variant CRNN cDNA (such as SEQ ID NO:6). In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, the isolated nucleic acid molecule comprises or consists of at least 15 nucleotides. In some embodiments, the isolated nucleic acid molecule comprises or consists of at least 15 nucleotides to at least about 35 nucleotides. In some embodiments, such isolated nucleic acid molecules hybridize to variant CRNN genomic DNA (such as SEQ ID NO:2), variant CRNN minigenes, variant CRNN mRNA (such as SEQ ID NO:4), and/or variant CRNN cDNA (such as SEQ ID NO:6) under stringent conditions. Such nucleic acid molecules may be used, for example, as probes, as primers, or as alteration-specific probes or primers as described or exemplified herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to variant CRNN genomic DNA (such as SEQ ID NO:2), variant CRNN minigenes, variant CRNN mRNA (such as SEQ ID NO:4), and/or variant CRNN cDNA (such as SEQ ID NO:6). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, any of the nucleic acid molecules, genomic DNA molecules, cDNA molecules, or mRNA molecules disclosed herein can be purified, e.g., are at least about 90% pure. In some embodiments, any of the nucleic acid molecules, genomic DNA molecules, cDNA molecules, or mRNA molecules disclosed herein can be purified, e.g., are at least about 95% pure. In some embodiments, any of the nucleic acid molecules, genomic DNA molecules, cDNA molecules, or mRNA molecules disclosed herein can be purified, e.g., are at least about 99% pure. Purification is according to the hands of a human being, with human-made purification techniques.

The present disclosure also provides fragments of any of the isolated nucleic acid molecules, genomic DNA molecules, cDNA molecules, or mRNA molecules disclosed herein. In some embodiments, the fragments comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous residues of any of the nucleic acid sequences disclosed herein, or any complement thereof. In this regard, the longer fragments are preferred over the shorter ones. In some embodiments, the fragments comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 contiguous residues. In this regard, the longer fragments are preferred over the shorter ones. In some embodiments, the fragments comprise or consist of at least about 20, at least about 25, at least about 30, or at least about 35 contiguous residues. In some embodiments, the fragments comprise or consist of at least about 20 contiguous residues. In some embodiments, the fragments comprise or consist of at least about 25 contiguous residues. In some embodiments, the fragments comprise or consist of at least about 30 contiguous residues. In some embodiments, the fragments comprise or consist of at least about 35 contiguous residues. It is envisaged that the fragments comprise of consist of the portion of the nucleic acid molecule that encodes a cysteine at a position corresponding to position 69 according to SEQ ID NO:8, or encodes positions corresponding to positions 69 to 79 according to SEQ ID NO:8. Such fragments may be used, for example, as probes, as primers, or as allele-specific primers as described or exemplified herein.

The present disclosure also provides a probe or a primer comprising a nucleic acid sequence comprising at least about 5 nucleotides, which hybridizes to a nucleic acid sequence encoding a human CRNN protein, wherein the protein is a loss-of-function CRNN protein or a CRNN protein truncated at a position corresponding to position 79 according to SEQ ID NO:8, or which hybridizes to the complement of the nucleic acid sequence encoding the human CRNN protein, wherein the protein is a loss-of-function CRNN protein or a CRNN protein truncated at a position corresponding to position 79 according to SEQ ID NO:8.

The present disclosure also provides probes and primers. The probe or primer of the present disclosure have a nucleic acid sequence that specifically hybridizes to any of the nucleic acid molecules disclosed herein, or the complement thereof. In some embodiments, the probe or primer specifically hybridizes to any of the nucleic acid molecules disclosed herein under stringent conditions. The present disclosure also provides nucleic acid molecules having nucleic acid sequences that hybridize under moderate conditions to any of the nucleic acid molecules disclosed herein, or the complement thereof. A probe or primer according to the disclosure preferably encompasses the nucleic acid codon which encodes the cysteine at a position corresponding to position 69 according to SEQ ID NO:8, or the complement thereof. Thus, in a preferred embodiment, the disclosure provides alteration-specific primers which are defined herein above and below in more detail.

A probe according to the present disclosure may be used to detect the variant CRNN nucleic acid molecule (e.g., genomic DNA, mRNA, and/or cDNA) encoding the variant CRNN protein (e.g., according to SEQ ID NO:8). In addition, a primer according to the present disclosure may be used to amplify a nucleic acid molecule encoding a variant CRNN protein, or fragment thereof. The disclosure also provides a pair of primers comprising one of the primers described above. For genomic polymerase chain reaction (PCR) amplification, suitable primer sequences include, but are not limited to regions of the CRNN fragment containing the frameshift variant leading to the truncation.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. MPSS can be used, for example, to determine expression levels of mRNA. mRNA are first converted to cDNA which are subsequently fused to a small oligonucleotide "tag" that allows the cDNA to be PCR amplified and then coupled to microbeads. Modified primers are used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. 454 Sequencing typically uses a large-scale parallel pyrosequencing system capable of sequencing roughly 400-600 megabases of DNA per 10-hour run on the Genome Sequencer FLX with GS FLX Titanium series reagents. Genomic DNA is fractionated into smaller fragments (e.g., 300-800 base pairs) and polished (made blunt at each end). Short adaptors can then be ligated onto the ends of the fragments. These adaptors provide priming sequences for both amplification and sequencing of the sample-library fragments. An adaptor can contain a 5'-biotin tag for immobilization of the DNA library onto streptavidin-coated beads.

The nucleic acid molecules disclosed herein can comprise a nucleic acid sequence of a naturally occurring CRNN genomic DNA, cDNA, or mRNA transcript, or can comprise a non-naturally occurring sequence. In some embodiments, the naturally occurring sequence can differ from the non-naturally occurring sequence due to synonymous mutations or mutations that do not affect the encoded CRNN polypeptide. For example, the sequence can be identical with the exception of synonymous mutations or mutations that do not affect the encoded CRNN polypeptide. A synonymous mutation or substitution is the substitution of one nucleotide for another in an exon of a gene coding for a protein such that the produced amino acid sequence is not modified. This is possible because of the degeneracy of the genetic code, with some amino acids being coded for by more than one three-base pair codon. Synonymous substitutions are used, for example, in the process of codon optimization. The nucleic acid molecules disclosed herein can be codon optimized.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant ($k_d$) less than or equal to about $10^{-6}$, less than or equal to about $10^{-8}$, less than or equal to about $10^{-10}$, or less than or equal to about $10^{-12}$. A representative sample of methods and techniques which aid in the design and use of antisense molecules can be found in the following non-limiting list of U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; and 6,057,437. Examples of antisense molecules include, but are not limited to, antisense RNAs, small interfering RNAs (siRNAs), and short hairpin RNAs (shRNAs).

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be in a vector or exogenous donor sequence comprising the isolated nucleic acid molecule and a heterologous nucleic acid sequence. The isolated nucleic acid molecules can also be linked or fused to a heterologous label, such as a fluorescent label. Other examples of labels are disclosed elsewhere herein.

The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, but are not limited to, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleotide analogs such as, for example, 5-substituted pyrimidines, 6-azapyrimidines, and N-2, N-6 and O-6 substituted purines including, but not limited to, 2-aminopropyladenine, 5-propynyluracil, 5-propynylcytosine, and 5-methylcytosine can increase the stability of duplex formation. Often, base modifications can be combined with, for example, a sugar modification, such as 2'-O-methoxyethyl, to achieve unique properties such as increased duplex stability.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[$(CH_2)_nO]_mCH_3$, —O$(CH_2)_nOCH_3$, —O$(CH_2)_nNH_2$, —O$(CH_2)_nCH_3$, —O$(CH_2)_n$—ONH$_2$, and —O$(CH_2)_nON[(CH_2)_nCH_3)]_2$, where n and m are from 1 to about 10.

Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included.

Nucleotide substitutes include molecules having similar functional properties to nucleotides, but which do not contain a phosphate moiety, such as peptide nucleic acid (PNA). Nucleotide substitutes include molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes also include nucleotides or nucleotide analogs that have had the phosphate moiety or sugar moieties replaced. In some embodiments, nucleotide substitutes may not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH$_2$ component parts.

It is also understood in a nucleotide substitute that both the sugar and the phosphate moieties of the nucleotide can be replaced by, for example, an amide type linkage (aminoethylglycine) (PNA).

It is also possible to link other types of molecules (conjugates) to nucleotides or nucleotide analogs to enhance, for example, cellular uptake. Conjugates can be chemically linked to the nucleotide or nucleotide analogs. Such conjugates include, for example, lipid moieties such as a cholesterol moiety, cholic acid, a thioether such as hexyl-S- tritylthiol, a thiocholesterol, an aliphatic chain such as dodecandiol or undecyl residues, a phospholipid such as di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety, or an octadecylamine or hexylamino-carbonyl-oxycholesterol moiety.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (e.g., a circular double-stranded DNA into which additional DNA segments can be ligated). In some embodiments, the vector is a viral vector, wherein additional DNA segments can be ligated into the viral genome. In some embodiments, the vector can autonomously replicate in a host cell into which it is introduced (e.g., bacterial vectors having a bacterial origin of replication and episomal mammalian vectors). In some embodiments, the vector (e.g., non-episomal mammalian vectors) can be integrated into the genome of a host cell upon introduction into the host cell and thereby are replicated along with the host genome. Moreover, particular vectors can direct the expression of genes to which they are operatively linked. Such vectors are referred to herein as "recombinant expression vectors" or "expression vectors." Such vectors can also be targeting vectors (i.e., exogenous donor sequences).

In some embodiments, the proteins encoded by the various genetic variants disclosed herein are expressed by inserting nucleic acid molecules encoding the disclosed genetic variants into expression vectors, such that the genes are operatively linked to expression control sequences, such as transcriptional and translational control sequences. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors. In some embodiments, nucleic acid molecules comprising the disclosed genetic variants can be ligated into a vector such that transcriptional and translational control sequences within the vector serve their intended function of regulating the transcription and translation of the genetic variant. The expression vector and expression control sequences are chosen to be compatible with the expression host cell used. Nucleic acid sequences comprising the disclosed genetic variants can be inserted into separate vectors or into the same expression vector as the variant genetic information. A nucleic acid sequence comprising the disclosed genetic variants can be inserted into the expression vector by standard methods (e.g., ligation of complementary restriction sites on the nucleic acid comprising the disclosed genetic variants and vector, or blunt end ligation if no restriction sites are present).

In addition to a nucleic acid sequence comprising the disclosed genetic variants, the recombinant expression vectors can carry regulatory sequences that control the expression of the genetic variant in a host cell. The design of the expression vector, including the selection of regulatory sequences can depend on such factors as the choice of the host cell to be transformed, the level of expression of protein desired, and so forth. Desired regulatory sequences for mammalian host cell expression can include, for example, viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. Polypeptides can be expressed in bacterial cells or fungal cells (e.g., yeast cells).

A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

In addition to a nucleic acid sequence comprising the disclosed genetic variants and regulatory sequences, the recombinant expression vectors can carry additional sequences, such as sequences that regulate replication of the vector in host cells (e.g., origins of replication) and selectable marker genes. A selectable marker gene can facilitate selection of host cells into which the vector has been introduced (see e.g., U.S. Pat. Nos. 4,399,216; 4,634,665; and 5,179,017). For example, a selectable marker gene can confer resistance to drugs, such as G418, hygromycin, or methotrexate, on a host cell into which the vector has been introduced. Exemplary selectable marker genes include, but are not limited to, the dihydrofolate reductase (DHFR) gene (for use in dhfr-host cells with methotrexate selection/amplification), the neo gene (for G418 selection), and the glutamate synthetase (GS) gene.

Additional vectors are described in, for example, U.S. Provisional Application No. 62/367,973, filed on Jul. 28, 2016, which is incorporated herein by reference in its entirety.

The present disclosure also provides compositions comprising any one or more of the isolated nucleic acid molecules, genomic DNA molecules, cDNA molecules, or mRNA molecules disclosed herein. In some embodiments, the composition is a pharmaceutical composition.

The present disclosure also provides isolated or recombinant polypeptides comprising at least a portion of the human CRNN protein, wherein the protein is a loss-offunction CRNN protein or a CRNN protein truncated at a position corresponding to position 79 according to SEQ ID NO:8.

The present disclosure also provides variant CRNN polypeptides. In some embodiments, the variant CRNN polypeptide is a loss-of-function protein. In some embodiments, the variant CRNN polypeptide is truncated. In some embodiments, the variant CRNN polypeptide is truncated at a position corresponding to position 79 according to SEQ ID NO:8. In some embodiments, the variant CRNN polypeptide is truncated at a position corresponding to position 79 according to SEQ ID NO:8, and comprises a cysteine at a position corresponding to position 69 according to SEQ ID NO:8. In some embodiments, the variant CRNN polypeptide is truncated at a position corresponding to position 79 according to SEQ ID NO:8, and comprises a plurality of the amino acids at positions corresponding to positions 69 to 79 according to SEQ ID NO:8. In some embodiments, the variant CRNN polypeptide is truncated at a position corresponding to position 79 according to SEQ ID NO:8, and comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the variant CRNN polypeptide has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:8, and comprises a cysteine at a position corresponding to position 69 according to SEQ ID NO:8. In some embodiments, the variant CRNN polypeptide comprises or consists of the amino acid sequence according to SEQ ID NO:8. In some embodiments, the truncated CRNN protein comprises or consists of the amino acid sequence according to SEQ ID NO:8, or an amino acid sequence that has at least 90% sequence identity to SEQ ID NO:9 and comprises a cysteine at a position corresponding to position 69 according to SEQ ID NO:8.

The present disclosure also provides fragments of any of the polypeptides disclosed herein. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, or at least about 75 contiguous amino acid residues of the encoded polypeptide (such as the polypeptide having the amino acid sequence of SEQ ID NO:8). In this regard, the longer fragments are preferred over the shorter ones.

The present disclosure also provides dimers comprising an isolated polypeptide comprising a variant CRNN polypeptide wherein the polypeptide is selected from any of the polypeptides disclosed herein.

In some embodiments, the isolated polypeptides disclosed herein are linked or fused to heterologous polypeptides or heterologous molecules or labels, numerous examples of which are disclosed elsewhere herein. For example, the proteins can be fused to a heterologous polypeptide providing increased or decreased stability. The fused domain or heterologous polypeptide can be located at the N-terminus, the C-terminus, or internally within the polypeptide. A fusion partner may, for example, assist in providing T helper epitopes (an immunological fusion partner), or may assist in expressing the protein (an expression enhancer) at higher yields than the native recombinant polypeptide. Certain fusion partners are both immunological and expression enhancing fusion partners. Other fusion partners may be selected to increase the solubility of the polypeptide or to facilitate targeting the polypeptide to desired intracellular compartments. Some fusion partners include affinity tags, which facilitate purification of the polypeptide.

In some embodiments, a fusion protein is directly fused to the heterologous molecule or is linked to the heterologous molecule via a linker, such as a peptide linker. Suitable peptide linker sequences may be chosen, for example, based on the following factors: 1) the ability to adopt a flexible extended conformation; 2) the resistance to adopt a secondary structure that could interact with functional epitopes on the first and second polypeptides; and 3) the lack of hydrophobic or charged residues that might react with the polypeptide functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in, for example, Maratea et al., *Gene*, 1985, 40, 39-46; Murphy et al., *Proc. Natl. Acad. Sci. USA*, 1986, 83, 8258-8262; and U.S. Pat. Nos. 4,935,233 and 4,751,180. A linker sequence may generally be, for example, from 1 to about 50 amino acids in length. Linker sequences are generally not required when the first and second polypeptides have non-essential N-terminal amino acid regions that can be used to separate the functional domains and prevent steric interference.

In some embodiments, the polypeptides are operably linked to a cell-penetrating domain. For example, the cell-penetrating domain can be derived from the HIV-1 TAT protein, the TLM cell-penetrating motif from human hepatitis B virus, MPG, Pep-1, VP22, a cell-penetrating peptide from Herpes simplex virus, or a polyarginine peptide sequence. See, e.g., WO 2014/089290. The cell-penetrating domain can be located at the N-terminus, the C-terminus, or anywhere within the protein.

In some embodiments, the polypeptides are operably linked to a heterologous polypeptide for ease of tracking or purification, such as a fluorescent protein, a purification tag, or an epitope tag. Examples of fluorescent proteins include, but are not limited to, green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include, but are not limited to, glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin. In some embodiments, the heterologous molecule is an immunoglobulin Fc domain, a peptide tag, a transduction domain, poly(ethylene glycol), polysialic acid, or glycolic acid.

In some embodiments, isolated polypeptides comprise non-natural or modified amino acids or peptide analogs. For example, there are numerous D-amino acids or amino acids which have a different functional substituent than the naturally occurring amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site-specific way.

In some embodiments, the isolated polypeptides are peptide mimetics, which can be produced to resemble peptides, but which are not connected via a natural peptide linkage. For example, linkages for amino acids or amino acid analogs include, but are not limited to, —CH$_2$NH—, —CH$_2$S—, —CH$_2$—, —CH=CH— (cis and trans), —COCH$_2$—, —CH(OH)CH$_2$—, and —CHH$_2$SO—. Peptide analogs can have more than one atom between the bond atoms, such as b-alanine, gaminobutyric acid, and the like. Amino acid analogs and peptide analogs often have enhanced or desirable properties, such as, more economical production, greater chemical stability, enhanced pharmacological properties (half-life, absorption, potency, efficacy, and so forth), altered specificity (e.g., a broad-spectrum of biological activities), reduced antigenicity, and others desirable properties.

In some embodiments, the isolated polypeptides comprise D-amino acids, which can be used to generate more stable peptides because D amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (see, e.g., Rizo and Gierasch, *Ann. Rev. Biochem.*, 1992, 61, 387).

The present disclosure also provides nucleic acid molecules encoding any of the polypeptides disclosed herein. This includes all degenerate sequences related to a specific polypeptide sequence (all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

Percent identity (or percent complementarity) between particular stretches of nucleic acid sequences within nucleic acids or amino acid sequences within polypeptides can be determined by using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the nucleic acid molecules and/or any one or more of the polypeptides disclosed herein and a carrier and/or excipient. In some embodiments, the carrier increases the stability of the nucleic acid molecule and/or polypeptide (e.g., prolonging the period under given conditions of storage (e.g., −20° C., 4° C., or ambient temperature) for which degradation products remain below a threshold, such as below 0.5% by weight of the starting nucleic acid or protein; or increasing the stability in vivo). Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

The present disclosure also provides methods of producing any of the polypeptides or fragments thereof disclosed herein. Such polypeptides or fragments thereof can be produced by any suitable method. For example, polypeptides or fragments thereof can be produced from host cells comprising nucleic acid molecules (e.g., recombinant expression vectors) encoding such polypeptides or fragments thereof. Such methods can comprise culturing a host cell comprising a nucleic acid molecule (e.g., recombinant expression vector) encoding a polypeptide or fragment thereof under conditions sufficient to produce the polypeptide or fragment thereof, thereby producing the polypeptide or fragment thereof. The nucleic acid can be operably linked to a promoter active in the host cell, and the culturing can be carried out under conditions whereby the nucleic acid is expressed. Such methods can further comprise recovering the expressed polypeptide or fragment thereof. The recovering can further comprise purifying the polypeptide or fragment thereof.

Examples of suitable systems for protein expression include host cells such as, for example: bacterial cell expression systems (e.g., *Escherichia coli, Lactococcus lactis*), yeast cell expression systems (e.g., *Saccharomyces cerevisiae, Pichia pastoris*), insect cell expression systems (e.g., baculovirus-mediated protein expression), and mammalian cell expression systems.

Examples of nucleic acid molecules encoding polypeptides or fragments thereof are disclosed in more detail elsewhere herein. In some embodiments, the nucleic acid molecules are codon optimized for expression in the host cell. In some embodiments, the nucleic acid molecules are operably linked to a promoter active in the host cell. The promoter can be a heterologous promoter (e.g., a promoter than is not a naturally occurring promoter). Examples of promoters suitable for *Escherichia coli* include, but are not limited to, arabinose, lac, tac, and T7 promoters. Examples of promoters suitable for *Lactococcus lactis* include, but are not limited to, P170 and nisin promoters. Examples of promoters suitable for *Saccharomyces cerevisiae* include, but are not limited to, constitutive promoters such as alcohol dehydrogenase (ADHI) or enolase (ENO) promoters or inducible promoters such as PHO, CUP1, GAL1, and G10. Examples of promoters suitable for *Pichia pastoris* include, but are not limited to, the alcohol oxidase I (AOX I) promoter, the glyceraldehyde 3 phosphate dehydrogenase (GAP) promoter, and the glutathione dependent formaldehyde dehydrogenase (FLDI) promoter. An example of a promoter suitable for a baculovirus-mediated system is the late viral strong polyhedrin promoter.

In some embodiments, the nucleic acid molecules encode a tag in frame with the polypeptide or fragment thereof to facilitate protein purification. Examples of tags are disclosed elsewhere herein. Such tags can, for example, bind to a partner ligand (e.g., immobilized on a resin) such that the tagged protein can be isolated from all other proteins (e.g., host cell proteins). Affinity chromatography, high performance liquid chromatography (HPLC), and size exclusion chromatography (SEC) are examples of methods that can be used to improve the purity of the expressed protein.

Other methods can also be used to produce polypeptides or fragments thereof. For example, two or more peptides or polypeptides can be linked together by protein chemistry techniques. For example, peptides or polypeptides can be chemically synthesized using either Fmoc (9-fluorenylmethyloxycarbonyl) or Boc (tert-butyloxycarbonoyl) chemistry. Such peptides or polypeptides can be synthesized by standard chemical reactions. For example, a peptide or polypeptide can be synthesized and not cleaved from its synthesis resin, whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively. Alternately, the peptide or polypeptide can be independently synthesized in vivo as described herein. Once isolated, these independent peptides or polypeptides may be linked to form a peptide or fragment thereof via similar peptide condensation reactions.

In some embodiments, enzymatic ligation of cloned or synthetic peptide segments allow relatively short peptide fragments to be joined to produce larger peptide fragments, polypeptides, or whole protein domains (Abrahmsen et al., *Biochemistry*, 1991, 30, 4151). Alternately, native chemical ligation of synthetic peptides can be utilized to synthetically construct large peptides or polypeptides from shorter peptide fragments. This method can consist of a two-step chemical reaction (Dawson et al., *Science*, 1994, 266, 776-779). The first step can be the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate can undergo spontaneous, rapid intramolecular reaction to form a native peptide bond at the ligation site.

In some embodiments, unprotected peptide segments can be chemically linked where the bond formed between the peptide segments as a result of the chemical ligation is an unnatural (non-peptide) bond (Schnolzer et al., *Science*, 1992, 256, 221).

In some embodiments, the polypeptides can possess post-expression modifications such as, for example, glycosylations, acetylations, and phosphorylations, as well as other modifications, both naturally occurring and non-naturally occurring. A polypeptide may be an entire protein, or a subsequence thereof.

The present disclosure also provides methods of producing any of the polypeptides disclosed herein, comprising culturing a host cell comprising a recombinant expression vectors comprising nucleic acid molecules comprising a polynucleotide capable of encoding one or more of the polypeptides disclosed herein, or its complement, thereby producing the polypeptide.

The present disclosure also provides cells (e.g., recombinant host cells) comprising any one or more of the nucleic acid molecules, including vectors comprising the nucleic acid molecules, and/or any one or more of the polypeptides disclosed herein. The cells can be in vitro, ex vivo, or in vivo. Nucleic acid molecules can be linked to a promoter and other regulatory sequences so they are expressed to produce an encoded protein. Cell lines of such cells are further provided.

In some embodiments, the cell is a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm). In accordance with the present disclosure, the embryonic stem cells may be non-human embryonic stem cells.

In some embodiments, the cell is a primary somatic cell, or a cell that is not a primary somatic cell. Somatic cells can include any cell that is not a gamete, germ cell, gametocyte, or undifferentiated stem cell. In some embodiments, the cell can also be a primary cell. Primary cells include cells or cultures of cells that have been isolated directly from an organism, organ, or tissue. Primary cells include cells that are neither transformed nor immortal. Primary cells include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

In some embodiments, the cells may normally not proliferate indefinitely but, due to mutation or alteration, have evaded normal cellular senescence and instead can keep undergoing division. Such mutations or alterations can occur naturally or be intentionally induced. Examples of immortalized cells include, but are not limited to, Chinese hamster ovary (CHO) cells, human embryonic kidney cells (e.g., HEK 293 cells), and mouse embryonic fibroblast cells (e.g., 3T3 cells). Numerous types of immortalized cells can be used. Immortalized or primary cells include cells that are typically used for culturing or for expressing recombinant genes or proteins. In some embodiments, the cell is a differentiated cell, such as a liver cell (e.g., a human liver cell).

The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, but are not limited to, chickens, turkeys, ostrich, geese, ducks, etc. Domesticated animals and agricultural animals are also included. The term "non-human animal" excludes humans.

Additional host cells are described in, for example, U.S. Provisional Application No. 62/367,973, filed on Jul. 28, 2016, which is incorporated herein by reference in its entirety.

The nucleic acid molecules and polypeptides disclosed herein can be introduced into a cell by any means. Transfection protocols as well as protocols for introducing nucleic acids or proteins into cells may vary. Non-limiting transfection methods include chemical-based transfection methods using liposomes, nanoparticles, calcium, dendrimers, and cationic polymers such as DEAE-dextran or polyethylenimine. Non-chemical methods include electroporation, sono-poration, and optical transfection. Particle-based transfection includes the use of a gene gun, or magnet-assisted transfection. Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In some embodiments, nucleofection is performed using the LONZA® NUCLEOFECTOR™ system.

Introduction of nucleic acids or proteins into a cell can also be accomplished by microinjection. Microinjection of an mRNA is usually into the cytoplasm (e.g., to deliver mRNA directly to the translation machinery), while microinjection of a protein or a DNA is usually into the nucleus. Alternately, microinjection can be carried out by injection into both the nucleus and the cytoplasm: a needle can first be introduced into the nucleus and a first amount can be injected, and while removing the needle from the cell a second amount can be injected into the cytoplasm. If a nuclease agent protein is injected into the cytoplasm, the protein may comprise a nuclear localization signal to ensure delivery to the nucleus/pronucleus.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein. Introduction of nucleic acids and proteins into cells can also be accomplished by hydrodynamic delivery (HDD).

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. In some embodiments, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

The present disclosure also provides probes and primers. Examples of probes and primers are disclosed above for example. The present disclosure provides probes and primers comprising a nucleic acid sequence that specifically hybridizes to any of the nucleic acid molecules disclosed herein. For example, the probe or primer may comprise a nucleic acid sequence which hybridizes to any of the nucleic acid molecules described herein that encode a variant CRNN protein that is truncated at a position corresponding to position 79 according to SEQ ID NO:8, or which hybridizes to the complement of the nucleic acid molecule. In some embodiments, the probe or primer comprises a nucleic acid sequence which hybridizes to a nucleic acid molecule encoding a variant CRNN protein according to SEQ ID NO:8, or which hybridizes to the complement of this nucleic acid molecule. In some embodiments, the probe or primer comprises a nucleic acid sequence which hybridizes to a nucleic acid molecule encoding a variant CRNN polypeptide that is truncated at a position corresponding to position 79 according to SEQ ID NO:8, and comprises a cysteine at a position corresponding to position 69 according to SEQ ID NO:8, or which hybridizes to the complement of this nucleic acid molecule. In some embodiments, the probe or primer comprises a nucleic acid sequence which hybridizes to a nucleic acid molecule encoding a variant CRNN polypeptide that is truncated at a position corresponding to position 79 according to SEQ ID NO:8, and comprises a plurality of the amino acids at positions corresponding to positions 69 to 79 according to SEQ ID NO:8, or which hybridizes to the complement of this nucleic acid molecule. In some embodiments, the probe or primer comprises a nucleic acid sequence which hybridizes to a nucleic acid molecule encoding a variant CRNN polypeptide that is truncated at a position corresponding to position 79 according to SEQ ID NO:8, and comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10), or which hybridizes to the complement of this nucleic acid molecule. In some embodiments, the probe or primer comprises a nucleic acid sequence which hybridizes to a nucleic acid molecule encoding a variant CRNN polypeptide that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:8 and comprises a cysteine at a position corresponding to position 69 according to SEQ ID NO:8, or which hybridizes to the complement of this nucleic acid molecule. In some embodiments, the probe or primer comprises a nucleic acid sequence which hybridizes to a nucleic acid molecule encoding a variant CRNN polypeptide that comprises or consists of the amino acid sequence according to SEQ ID NO:8, or which hybridizes to the complement of this nucleic acid molecule. In some embodiments, the probe or primer specifically hybridizes to a portion of the nucleic acid molecule encompassing the codon which encodes a cysteine at the position corresponding to the position 69 according to SEQ ID NO:8.

The probe or primer may comprise any suitable length, non-limiting examples of which include at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. In preferred embodiments, the probe or primer comprises at least about 18 nucleotides in length. The probe or primer may comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In preferred embodiments, the probe or primer is from about 18 to about 30 nucleotides in length.

The present disclosure also provides an alteration-specific probe or primer comprising a nucleic acid sequence which is complementary to a nucleic acid sequence encoding a loss-of-function CRNN protein or CRNN protein truncated at a position corresponding to position 79 according to SEQ ID NO:8, wherein the alteration-specific probe or primer comprises a nucleic acid sequence which is complementary to a portion of the nucleic acid molecule encoding any plurality of positions corresponding to positions 69 to 76, 78, or 79 according to SEQ ID NO:8. In some embodiments, the alteration-specific probe or primer specifically hybridizes to a portion of the nucleic acid molecule encoding a position corresponding to position 69 according to SEQ ID NO:8, or to the complement thereof. The alteration-specific probe or primer does not hybridize to a nucleic acid molecule having a nucleic acid sequence encoding a wild-type CRNN protein.

The present disclosure also provides alteration-specific probes and alteration-specific primers. The alteration-specific probe or alteration-specific primer comprises a nucleic acid sequence which is complementary to and/or hybridizes, or specifically hybridizes, to a nucleic acid sequence encoding a variant CRNN protein that is truncated at a position corresponding to position 79 according to SEQ ID NO:8, or to the complement thereof. In the context of the disclosure "specifically hybridizes" means that the probe or primer (e.g., the alteration-specific probe or alteration-specific primer) does not hybridize to a nucleic acid molecule encoding wild type CRNN protein. In some embodiments, the alteration-specific probe specifically hybridizes to the nucleic acid codon which encodes the cysteine at a position corresponding to position 69 according to SEQ ID NO:8, or the complement thereof. In some embodiments, the alteration-specific primer, or primer pair, specifically hybridizes to a region(s) of the nucleic acid molecule encoding a variant CRNN protein such that the codon which encodes the cysteine at a position corresponding to position 69 according to SEQ ID NO:8 is encompassed within any transcript produced therefrom. In some embodiments, the probe or primer specifically hybridizes to a portion of the nucleic acid molecule encompassing the codon which encodes a cysteine at the position corresponding to the position 69 according to SEQ ID NO:8.

In some embodiments, the alteration-specific probe or alteration-specific primer comprises a nucleic acid sequence which is complementary to and/or hybridizes, or specifically hybridizes, to a nucleic acid sequence encoding a variant CRNN protein, wherein the protein comprises a truncation at a position corresponding to position 79 according to SEQ ID NO:8, or the complement thereof.

In some embodiments, the alteration-specific probe or alteration-specific primer comprises a nucleic acid sequence which is complementary to and/or hybridizes, or specifically hybridizes, to a genomic DNA molecule encoding a variant CRNN protein truncated at a position corresponding to position 79 according to SEQ ID NO:8, or the complement thereof. In some embodiments, the alteration-specific probe or alteration-specific primer comprises a nucleic acid sequence which is complementary to and/or hybridizes, or specifically hybridizes, to a genomic DNA molecule encoding a variant CRNN protein truncated at a position corresponding to position 79 according to SEQ ID NO:8, and that comprises a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to a genomic DNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the alteration-specific probe or alteration-specific primer comprises a nucleic acid sequence which is complementary to and/or hybridizes, or specifically hybridizes, to a genomic DNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to a genomic DNA molecule encoding a variant CRNN protein having SEQ ID NO:8. In some embodiments, the probe or primer specifically hybridizes to a portion of the genomic DNA encompassing the codon which encodes a cysteine at the position corresponding to the position 69 according to SEQ ID NO:8.

In some embodiments, the alteration-specific probe or alteration-specific primer comprises a nucleic acid sequence which is complementary to and/or hybridizes, or specifically hybridizes, to a genomic DNA molecule that comprises or consists of a nucleic acid sequence comprising a thymine at a position corresponding to position 3375 according to SEQ ID NO:2. In some embodiments, the alteration-specific probe or alteration-specific primer comprises a nucleic acid sequence which is complementary to and/or hybridizes, or specifically hybridizes, to a genomic DNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a thymine at a position corresponding to position 3375 according to SEQ ID NO:2. In some embodiments, the alteration-specific probe or alteration-specific primer comprises a nucleic acid sequence which is complementary to and/or hybridizes, or specifically hybridizes, to a genomic DNA molecule that comprises or consists of a nucleic acid sequence according to SEQ ID NO:2.

In some embodiments, the alteration-specific probe or alteration-specific primer comprises a nucleic acid sequence which is complementary to and/or hybridizes, or specifically hybridizes, to an mRNA molecule encoding a variant CRNN protein truncated at a position corresponding to position 79 according to SEQ ID NO:8. In some embodiments, the alteration-specific probe or alteration-specific primer comprises a nucleic acid sequence which is complementary to and/or hybridizes, or specifically hybridizes, to an mRNA molecule encoding a variant CRNN protein truncated at a position corresponding to position 79 according to SEQ ID NO:8, and that comprises a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to an mRNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the alteration-specific probe or alteration-specific primer comprises a nucleic acid sequence which is complementary to and/or hybridizes, or specifically hybridizes, to an mRNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to an mRNA molecule encoding a variant CRNN protein having SEQ ID NO:8. In some embodiments, the probe or primer specifically hybridizes to a portion of the mRNA molecule encompassing the codon which encodes a cysteine at the position corresponding to the position 69 according to SEQ ID NO:8.

In some embodiments, the alteration-specific probe or alteration-specific primer comprises a nucleic acid sequence which is complementary to and/or hybridizes, or specifically hybridizes, to an mRNA molecule that comprises or consists of a nucleic acid sequence comprising a uracil at a position corresponding to position 205 according to SEQ ID NO:4. In some embodiments, the alteration-specific probe or alteration-specific primer comprises a nucleic acid sequence which is complementary to and/or hybridizes, or specifically hybridizes, to an mRNA molecule that comprises the codons ACU and UGU at positions corresponding to positions 202 to 204 and 205 to 207, respectively, according to SEQ ID NO:4. In some embodiments, the alteration-specific probe or alteration-specific primer comprises a nucleic acid sequence which is complementary to and/or hybridizes, or specifically hybridizes, to an mRNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises a uracil at a position corresponding to position 205 according to SEQ ID NO:4. In some embodiments, the alteration-specific probe or alteration-specific primer comprises a nucleic acid sequence which is complementary to and/or hybridizes, or specifically hybridizes, to an mRNA molecule that comprises or consists of a nucleic acid sequence according to SEQ ID NO:4.

In some embodiments, the alteration-specific probe or alteration-specific primer comprises a nucleic acid sequence which is complementary to and/or hybridizes, or specifically hybridizes, to a cDNA molecule encoding a variant CRNN protein truncated at a position corresponding to position 79 according to SEQ ID NO:8. In some embodiments, the alteration-specific probe or alteration-specific primer comprises a nucleic acid sequence which is complementary to and/or hybridizes, or specifically hybridizes, to a cDNA molecule encoding a variant CRNN protein truncated at a position corresponding to position 79 according to SEQ ID NO:8, and that comprises a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to a cDNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the alteration-specific probe or alteration-specific primer comprises a nucleic acid sequence which is complementary to and/or hybridizes, or specifically hybridizes, to a cDNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprising a cysteine at a position corresponding to position 69 according to SEQ ID NO:8. In some embodiments, the alteration-specific probe or alteration-specific primer comprises a nucleic acid sequence which is complementary to and/or hybridizes, or specifically hybridizes, to a cDNA molecule encoding a variant CRNN protein having SEQ ID NO:8. In some embodiments, the probe or primer specifically hybridizes to a portion of the cDNA molecule encompassing the codon which encodes a cysteine at the position corresponding to the position 69 according to SEQ ID NO:8.

In some embodiments, the alteration-specific probe or alteration-specific primer comprises a nucleic acid sequence which is complementary to and/or hybridizes, or specifically hybridizes, to an cDNA molecule that comprises or consists of a nucleic acid sequence comprising a thymine at a position corresponding to position 205 according to SEQ ID NO:6. In some embodiments, the alteration-specific probe or alteration-specific primer comprises a nucleic acid sequence which is complementary to and/or hybridizes, or specifically hybridizes, to a cDNA molecule that comprises the codons ACT and TGT at positions corresponding to positions 202 to 204 and 205 to 207, respectively, according to SEQ ID NO:6. In some embodiments, the alteration-specific probe or alteration-specific primer comprises a nucleic acid sequence which is complementary to and/or hybridizes, or specifically hybridizes, to a cDNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises a thymine at a position corresponding to position 205 according to SEQ ID NO:6. In some embodiments, the alteration-specific probe or alteration-specific primer comprises a nucleic acid sequence which is complementary to and/or hybridizes, or specifically hybridizes, to a cDNA molecule that comprises or consists of a nucleic acid sequence according to SEQ ID NO:6.

The length which is described above with regard to the probe or primer of the disclosure applies, mutatis mutandis, also for the alteration-specific probe or alteration-specific primer of the disclosure.

The disclosure also provides a pair of alteration-specific primers comprising two of the alteration-specific primers as described above.

In some embodiments, the probe or primer (e.g., the alteration-specific probe or alteration-specific primer) comprises DNA. In some embodiments, the probe or primer (e.g., alteration-specific probe or alteration-specific primer)

comprises RNA. In some embodiments, the probe or primer (e.g., the alteration-specific probe or alteration-specific primer) hybridizes to a nucleic acid sequence encoding the variant CRNN protein under stringent conditions, such as high stringent conditions.

In some embodiments, the probe comprises a label. In some embodiments, the label is a fluorescent label, a radio-label, or biotin. In some embodiments, the length of the probe is described above. Alternately, in some embodiments, the probe comprises or consists of at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides. The probe (e.g., the allele-specific probe) may be used, for example, to detect any of the nucleic acid molecules disclosed herein. In preferred embodiments, the probe comprises at least about 18 nucleotides in length. The probe may comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In preferred embodiments, the probe is from about 18 to about 30 nucleotides in length.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A form for a solid-state substrate is a microtiter dish, such as a standard 96-well type. In some embodiments, a multiwell glass slide can be employed that normally contain one array per well. This feature allows for greater control of assay reproducibility, increased throughput and sample handling, and ease of automation. In some embodiments, the support is a microarray.

Any of the polypeptides disclosed herein can further have one or more substitutions (such as conservative amino acid substitutions), insertions, or deletions. Insertions include, for example, amino or carboxyl terminal fusions as well as intrasequence insertions of single or multiple amino acid residues. Techniques for making substitutions at predetermined sites in DNA having a known sequence include, but are not limited to, M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e. a deletion of 2 residues or insertion of 2 residues. Substitutions, deletions, insertions or any combination thereof may be combined to arrive at a final construct. In some embodiments, the mutations do not place the sequence out of reading frame and do not create complementary regions that could produce secondary mRNA structure.

The present disclosure also provides kits for making the compositions and utilizing the methods described herein. The kits described herein can comprise an assay or assays for detecting one or more genetic variants in a sample of a subject.

In some embodiments, the kits for human identification of CRNN variants utilize the compositions and methods described above. In some embodiments, a basic kit can comprise a container having at least one pair of oligonucleotide primers or probes, such as alteration-specific probes or alteration-specific primers, for a locus in any of the nucleic acid molecules disclosed herein (such as, for example, SEQ ID NO:2, SEQ ID NO:4, and/or SEQ ID NO:6). A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers.

In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule encoding a variant CRNN protein truncated at a position corresponding to position 79 according to SEQ ID NO:8, or the complement thereof. In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule encoding a variant CRNN protein truncated at a position corresponding to position 79 according to SEQ ID NO:8, and that comprises a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprising a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule encoding a variant CRNN protein having SEQ ID NO:8.

In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule that comprises or consists of a nucleic acid sequence comprising a thymine at a position corresponding to position 3375 according to SEQ ID NO:2. In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a thymine at a position corresponding to position 3375 according to SEQ ID NO:2. In some embodiments, the kits comprise at least one pair of oligonucleotide primers (e.g., alteration-specific primers) for amplification, or at least one labeled oligonucleotide probe (e.g., alteration-specific probe) for detection, of a genomic DNA molecule that comprises or consists of a nucleic acid sequence according to SEQ ID NO:2.

In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule encoding a variant CRNN protein truncated at a position corresponding to position 79 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule encoding a variant CRNN protein truncated at a position corresponding to position 79 according to SEQ ID NO:8, and that comprises a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprising a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule encoding a variant CRNN protein having SEQ ID NO:8.

In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule that comprises or consists of a nucleic acid sequence comprising a uracil at a position corresponding to position 205 according to SEQ ID NO:4. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule that comprises the codons ACU and UGU at positions corresponding to positions 202 to 204 and 205 to 207, respectively, according to SEQ ID NO:4. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4, and comprises a uracil at a position corresponding to position 205 according to SEQ ID NO:4. In some embodiments, the kits comprise at least one pair of oligonucleotide primers (e.g., alteration-specific primers) for amplification, or at least one labeled oligonucleotide probe (e.g., alteration-specific probe) for detection, of an mRNA molecule that comprises or consists of a nucleic acid sequence according to SEQ ID NO:4.

In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule encoding a variant CRNN protein truncated at a position corresponding to position 79 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule encoding a variant CRNN protein truncated at a position corresponding to position 79 according to SEQ ID NO:8, and that comprises a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule encoding a variant CRNN protein truncated at a position corresponding to position 79 according to SEQ ID NO:8, and that comprises the following amino acid sequence at positions corresponding to positions 69 to 79 according to SEQ ID NO:8: Cys-Gly-Ile-Gln-Gly-Ile-Pro-Gly-Leu-Ser-Val (SEQ ID NO:10). In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule encoding a variant CRNN protein having at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprises a cysteine at a position corresponding to position 69 according to SEQ ID NO:8. In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule encoding a variant CRNN protein having SEQ ID NO:8.

In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule that comprises or consists of a nucleic acid sequence comprising a thymine at a position corresponding to position 205 according to SEQ ID NO:6. In some embodiments, the kits comprise at least one pair of oligonucleotide primers (e.g., alteration-specific primers) for amplification, or at least one labeled oligonucleotide probe (e.g., alteration-specific probe) for detection, of a cDNA molecule that comprises the codons ACT and TGT at positions corresponding to positions 202 to 204 and 205 to 207, respectively, according to SEQ ID NO:6. In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule that comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises a thymine at a position corresponding to position 205 according to SEQ ID NO:6. In some embodiments, the kits comprise at least one pair of oligonucleotide primers (e.g., alteration-specific primers) for amplification, or at least one labeled oligonucleotide probe (e.g., alteration-specific probe) for detection, of an cDNA molecule that comprises or consists of a nucleic acid sequence according to SEQ ID NO:6.

In some embodiments, any of the kits disclosed herein may further comprise any one or more of: a nucleotide ladder, protocol, an enzyme (such as an enzyme used for amplification, such as polymerase chain reaction (PCR)), dNTPs, a buffer, a salt or salts, and a control nucleic acid sample. In some embodiments, any of the kits disclosed herein may further comprise any one or more of: a detectable label, products and reagents required to carry out an annealing reaction, and instructions.

In some embodiments, the kits disclosed herein can comprise a primer or probe or an alteration-specific primer or an alteration-specific probe comprising a 3' terminal nucleotide that hybridizes directly to a thymine at a position corresponding to position 3375 of SEQ ID NO:2, or at a position corresponding to position 205 of SEQ ID NO:4 and/or SEQ ID NO:6.

Those in the art understand that the detection techniques employed are generally not limiting. Rather, a wide variety of detection means are within the scope of the disclosed methods and kits, provided that they allow the presence or absence of an amplicon to be determined.

In some aspects, a kit can comprise one or more of the primers or probes disclosed herein. For example, a kit can comprise one or more probes that hybridize to one or more of the disclosed genetic variants.

In some aspects, a kit can comprise one of the disclosed cells or cell lines. In some aspects, a kit can comprise the materials necessary to create a transgenic cell or cell line. For example, in some aspects a kit can comprise a cell and a vector comprising a nucleic acid sequence comprising one or more of the disclosed genetic variants. A kit can further comprise media for cell culture.

The present disclosure also provides methods for detecting the presence of a CRNN variant genomic DNA, mRNA, cDNA, and/or polypeptide in a biological sample from a subject human. It is understood that gene sequences within a population and mRNAs and proteins encoded by such genes can vary due to polymorphisms such as single-nucleotide polymorphisms. The sequences provided herein for the CRNN genomic DNA, mRNA, cDNA, and polypeptide are only exemplary sequences. Other sequences for the CRNN genomic DNA, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant CRNN nucleic acid molecule, preliminary processing designed to isolate or enrich the sample for the genomic DNA can be employed. A variety of techniques may be used for this purpose. When detecting the level of variant CRNN mRNA, different techniques can be used enrich the biological sample with mRNA. Various methods to detect the presence or level of a mRNA or the presence of a particular variant genomic DNA locus can be used.

In some embodiments, the disclosure provides methods of detecting the presence or absence of a variant CRNN protein comprising sequencing at least a portion of a protein in a biological sample to determine whether the protein comprises an amino acid sequence encoding a loss-of-function CRNN protein or a truncated CRNN protein. In some embodiments, the disclosure provides methods of detecting the presence or absence of a loss-of-function CRNN protein or a variant CRNN protein comprising sequencing at least a portion of a protein in a biological sample to determine whether the protein comprises an amino acid sequence encoding a CRNN protein truncated at a position corresponding to position 79 according to SEQ ID NO:8. In some embodiments, the disclosure provides methods of detecting the presence or absence of a variant CRNN protein comprising sequencing at least a portion of a protein in a biological sample to determine whether the protein comprises an amino acid sequence encoding a CRNN protein truncated at a position corresponding to position 79 according to SEQ ID NO:8, and comprises a cysteine at the position corresponding to position 69 according to SEQ ID NO:8.

In some embodiments, the disclosure provides methods of detecting the presence or absence of a variant CRNN nucleic acid molecule comprising sequencing at least a portion of a nucleic acid in a biological sample to determine whether the nucleic acid comprises a nucleic acid sequence encoding a loss-of-function CRNN protein or a truncated CRNN protein. In some embodiments, the disclosure provides methods of detecting the presence or absence of a variant CRNN nucleic acid molecule comprising sequencing at least a portion of a nucleic acid in a biological sample to determine whether the nucleic acid comprises a nucleic acid sequence encoding a CRNN protein truncated at a position corresponding to position 79 according to SEQ ID NO:8. In some embodiments, the disclosure provides methods of detecting the presence or absence of a variant CRNN nucleic acid molecule comprising sequencing at least a portion of a nucleic acid in a biological sample to determine whether the nucleic acid comprises a nucleic acid sequence encoding a CRNN protein truncated at a position corresponding to position 79 according to SEQ ID NO:8, and comprises a cysteine at the position corresponding to position 69 according to SEQ ID NO:8. Any of the variant nucleic acid molecules disclosed herein can be detected using any of the probes and primers described herein.

In some embodiments, the methods of detecting the presence or absence of a skin disorder-associated variant CRNN nucleic acid molecule (e.g., genomic DNA, mRNA, or cDNA) in a subject, comprising: performing an assay on a biological sample obtained from the subject, which assay determines whether a nucleic acid molecule in the biological sample comprises any of the variant CRNN nucleic acid sequences disclosed herein (e.g., a nucleic acid molecule that encodes a loss-of-function CRNN protein, a nucleic acid molecule that encodes a truncated CRNN protein, a nucleic acid molecule that encodes a CRNN protein truncated at a position corresponding to position 79 according to SEQ ID NO:8, a nucleic acid molecule that encodes a CRNN protein truncated at a position corresponding to position 79 according to SEQ ID NO:8 and comprising a cysteine at the position corresponding to position 69 according to SEQ ID NO:8). In some embodiments, the biological sample comprises a cell or cell lysate. Such methods can further comprise, for example, obtaining a biological sample from the subject comprising a CRNN genomic DNA or mRNA, and if mRNA, optionally reverse transcribing the mRNA into cDNA, and performing an assay on the biological sample that determine whether a position of the CRNN genomic DNA, mRNA, or cDNA encodes a truncated CRNN protein. Such methods can further comprise, for example, obtaining a biological sample from the subject comprising a CRNN genomic DNA or mRNA, and if mRNA, optionally reverse transcribing the mRNA into cDNA, and performing an assay on the biological sample that determine whether a position of the CRNN genomic DNA, mRNA, or cDNA encodes a CRNN protein truncated at a position corresponding to position 79 according to SEQ ID NO:8, or performing an assay on the biological sample that determine whether a position of the CRNN genomic DNA, mRNA, or cDNA encodes a CRNN protein truncated at a position corresponding to position 79 according to SEQ ID NO:8 and comprising a cysteine at the position corresponding to position 69 according to SEQ ID NO:8. Such assays can comprise, for example determining the identity of these positions of the particular CRNN nucleic acid molecule. In some embodiments, the subject is a human.

In some embodiments, the assay comprises: sequencing at least a portion of the CRNN genomic DNA sequence of a nucleic acid molecule in the biological sample from the subject, wherein the portion sequenced includes the position corresponding to the position encoding a cysteine at position 69 in the CRNN protein according to SEQ ID NO:8; sequencing at least a portion of the CRNN mRNA sequence of a nucleic acid molecule in the biological sample from the subject, wherein the portion sequenced includes the position corresponding to the position encoding a cysteine at position 69 in the CRNN protein according to SEQ ID NO:8; or sequencing at least a portion of the CRNN cDNA sequence of a nucleic acid molecule in the biological sample from the subject, wherein the portion sequenced includes the position corresponding to the position encoding a cysteine at position 69 in the CRNN protein according to SEQ ID NO:8.

In some embodiments, the assay comprises: a) contacting the biological sample with a primer hybridizing to: i) a portion of the CRNN genomic DNA sequence that is proximate to a position of the CRNN genomic sequence at the position corresponding to the position encoding a cysteine at position 69 according to SEQ ID NO:8; ii) a portion of the CRNN mRNA sequence that is proximate to a position of the CRNN mRNA sequence at the position corresponding to the position encoding a cysteine at position 69 according to SEQ ID NO:8; or iii) a portion of the CRNN cDNA sequence that is proximate to a position of the CRNN cDNA sequence at the position corresponding to the position encoding a cysteine at position 69 according to SEQ ID NO:8; b) extending the primer at least through: i) the position of the CRNN genomic DNA sequence corresponding to nucleotide positions beyond the codon encoding a cysteine at position 69 according to SEQ ID NO:8; ii) the position of the CRNN mRNA sequence corresponding to nucleotide positions beyond the codon encoding a cysteine at position 69 according to SEQ ID NO:8; or iii) the position of the CRNN cDNA sequence corresponding to nucleotide positions beyond the codon encoding a cysteine at position 69 according to SEQ ID NO:8; and c) determining whether the extension product of the primer comprises nucleotides encoding a cysteine at the position corresponding to position 69 according to SEQ ID NO:8. In some embodiments, only CRNN genomic DNA is analyzed. In some embodiments, only CRNN mRNA is analyzed. In some embodiments, only CRNN cDNA obtained from CRNN mRNA is analyzed.

In some embodiments, the assay comprises: a) contacting the biological sample with an alteration-specific primer hybridizing to i) a portion of the CRNN genomic DNA sequence including the nucleotides encoding a cysteine at the position corresponding to position 69 according to SEQ ID NO:8; ii) a portion of the CRNN mRNA sequence including the nucleotides encoding a cysteine at the position corresponding to position 69 according to SEQ ID NO:8; or iii) a portion of the CRNN cDNA sequence including the nucleotides encoding a cysteine at the position corresponding to position 69 according to SEQ ID NO:8; b) extending the primer using an alteration-specific polymerase chain reaction technique; and c) determining whether extension occurred. Alteration-specific polymerase chain reaction techniques can be used to detect mutations such as deletions in a nucleic acid sequence. Alteration-specific primers are used because the DNA polymerase will not extend when a mismatch with the template is present. A number of variations of the basic alteration-specific polymerase chain reaction technique are at the disposal of the skilled artisan.

The alteration-specific primer may comprise a nucleic acid sequence which is complementary to a nucleic acid sequence encoding the CRNN protein comprising a cysteine at the position corresponding to position 69 according to SEQ ID NO:8, or the complement to the nucleic acid sequence. For example, the alteration-specific primer may comprise a nucleic acid sequence which is complementary to the nucleic acid sequence encoding SEQ ID NO:8, or to the complement to this nucleic acid sequence. The alteration-specific primer preferably specifically hybridizes to the nucleic acid sequence encoding the variant CRNN protein when the nucleic acid sequence encodes a cysteine at the position corresponding to position 69 according to SEQ ID NO:8.

In some embodiments, the assay comprises contacting the biological sample with a primer or probe that specifically hybridizes to a variant CRNN genomic DNA sequence, mRNA sequence, or cDNA sequence and not the corresponding wild type CRNN sequence under stringent conditions, and determining whether hybridization has occurred.

In some embodiments, the assay comprises RNA sequencing (RNA-Seq). In some embodiments, the assays also comprise reverse transcribing mRNA into cDNA via the reverse transcriptase polymerase chain reaction (RT-PCR).

In some embodiments, the methods utilize probes and primers of sufficient nucleotide length to bind to the target nucleic acid sequence and specifically detect and/or identify a polynucleotide comprising a variant CRNN genomic DNA, mRNA, or cDNA. The hybridization conditions or reaction conditions can be determined by the operator to achieve this result. This nucleotide length may be any length that is sufficient for use in a detection method of choice, including any assay described or exemplified herein. Generally, for example, primers or probes having about 8, about 10, about 11, about 12, about 14, about 15, about 16, about 18, about 20, about 22, about 24, about 26, about 28, about 30, about 40, about 50, about 75, about 100, about 200, about 300, about 400, about 500, about 600, or about 700 nucleotides, or more, or from about 11 to about 20, from about 20 to about 30, from about 30 to about 40, from about 40 to about 50, from about 50 to about 100, from about 100 to about 200, from about 200 to about 300, from about 300 to about 400, from about 400 to about 500, from about 500 to about 600, from about 600 to about 700, or from about 700 to about 800, or more nucleotides in length are used. In preferred embodiments, the probe or primer comprises at least about 18 nucleotides in length. The probe or primer may comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In preferred embodiments, the probe or primer is from about 18 to about 30 nucleotides in length.

Such probes and primers can hybridize specifically to a target sequence under high stringency hybridization conditions. Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the target nucleic acid molecule.

In some embodiments, specific primers can be used to amplify the variant CRNN locus and/or CRNN variant mRNA or cDNA to produce an amplicon that can be used as a specific probe or can itself be detected for identifying the variant CRNN locus or for determining the level of specific CRNN mRNA or cDNA in a biological sample. The CRNN variant locus can be used to denote a genomic nucleic acid sequence including positions corresponding to positions encoding a cysteine at the position corresponding to position 69 according to SEQ ID NO:8. When the probe is hybridized with a nucleic acid molecule in a biological sample under conditions that allow for the binding of the probe to the nucleic acid molecule, this binding can be detected and allow for an indication of the presence of the variant CRNN locus or the presence or the level of variant CRNN mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant CRNN gene. The specific probe may comprise a sequence of at least about 80%, from about 80% to about 85%, from about 85% to about 90%, from about 90% to about 95%, and from about 95% to about 100% identical (or complementary) to a specific region of a variant CRNN mRNA. The specific probe may comprise a sequence of at least about 80%, from about 80% to about 85%, from about 85% to about 90%, from about 90% to about 95%, and from about 95% to about 100% identical (or complementary) to a specific region of a variant CRNN cDNA.

In some embodiments, to determine whether the nucleic acid complement of a biological sample comprises a nucleic acid sequence encoding the variant CRNN protein (e.g., a loss-of-function CRNN protein, a truncated CRNN protein, or a variant CRNN protein having a cysteine at the position corresponding to position 69 according to SEQ ID NO:8), the biological sample may be subjected to a nucleic acid amplification method using a primer pair that includes a first primer derived from the 5' flanking sequence adjacent to positions encoding the serine at the position corresponding to position 69 according to SEQ ID NO:8, and a second primer derived from the 3' flanking sequence adjacent to positions encoding the cysteine at the position corresponding to position 69 according to SEQ ID NO:8, to produce an amplicon that is diagnostic for the presence of the nucleotides at positions encoding the cysteine at the position corresponding to position 69 according to SEQ ID NO:8. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding the cysteine at position 69 according to SEQ ID NO:8 and at least 1, 2, 3, 4, 5, 6, 7, 8, 9, 10, or more nucleotides on each side of positions encoding the cysteine at position 69 according to SEQ ID NO:8. Similar amplicons can be generated from the mRNA and/or cDNA sequences.

Representative methods for preparing and using probes and primers are described, for example, in *Molecular Cloning: A Laboratory Manual,* 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified.

Any nucleic acid hybridization or amplification or sequencing method can be used to specifically detect the presence of the variant CRNN gene locus and/or the level of variant CRNN mRNA or cDNA produced from mRNA. In some embodiments, the nucleic acid molecule can be used either as a primer to amplify a region of the CRNN nucleic acid or the nucleic acid molecule can be used as a probe that specifically hybridizes, for example, under stringent conditions, to a nucleic acid molecule comprising the variant CRNN gene locus or a nucleic acid molecule comprising a variant CRNN mRNA or cDNA produced from mRNA.

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, methods of Southern (DNA:DNA) blot hybridizations, in situ hybridization (ISH), and fluorescence in situ hybridization (FISH) of chromosomal material. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected. In any such methods, the process can include hybridization using any of the probes described or exemplified herein.

In hybridization techniques, stringent conditions can be employed such that a probe or primer will specifically hybridize to its target. In some embodiments, a polynucleotide primer or probe under stringent conditions will hybridize to its target sequence (e.g., the variant CRNN gene locus, variant CRNN mRNA, or variant CRNN cDNA) to a detectably greater degree than to other sequences (e.g., the corresponding wild type CRNN locus, wild type mRNA, or wild type cDNA), such as, at least 2-fold, at least 3-fold, at least 4-fold, or more over background, including over 10-fold over background. In some embodiments, a polynucleotide primer or probe under stringent conditions will hybridize to its target sequence to a detectably greater degree than to other sequences by at least 2-fold. In some embodiments, a polynucleotide primer or probe under stringent conditions will hybridize to its target sequence to a detectably greater degree than to other sequences by at least 3-fold. In some embodiments, a polynucleotide primer or probe under stringent conditions will hybridize to its target sequence to a detectably greater degree than to other sequences by at least 4-fold. In some embodiments, a polynucleotide primer or probe under stringent conditions will hybridize to its target sequence to a detectably greater degree than to other sequences by over 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing).

Appropriate stringency conditions which promote DNA hybridization include, but are not limited to, 6× sodium chloride/sodium citrate (SSC) at about 45° C., followed by a wash of 2×SSC at 50° C., and conditions disclosed in, for example, Current Protocols in Molecular Biology, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 1984, 138, 267-284:$T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7° C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used.

Also provided are methods for detecting the presence or quantifying the levels of variant CRNN polypeptide in a biological sample, including, for example, protein sequencing and immunoassays. In some embodiments, the method of detecting the presence of variant CRNN protein (e.g., SEQ ID NO:8) in a human subject comprises performing an assay on a biological sample from the human subject that detects the presence of the variant CRNN protein (e.g., SEQ ID NO:8) in the biological sample.

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various techniques (e.g., calorimetric, fluorescent, chemiluminescent, or radioactive) are suitable for use in the immunoassays. Regarding immunoassays, the variant CRNN protein has a different size as compared to the wild type CRNN protein and, therefore, runs at a different molecular weight on a protein gel. Thus, by using the same antibody, the wild type CRNN protein can be distinguished from the variant CRNN protein in, for example, a Western Blot assay.

The present disclosure also provides methods for diagnosing a skin disorder or detecting a risk of developing a skin disorder in a human subject, comprising: detecting an alteration in a nucleic acid molecule encoding a CRNN protein obtained from the human subject, wherein the alteration encodes a loss-of-function CRNN protein or a truncated CRNN protein; and diagnosing the human subject with a skin disorder if the subject has one or more symptoms of a skin disorder, or diagnosing the human subject as at risk for developing a skin disorder if the subject does not have one or more symptoms of a skin disorder.

The present disclosure also provides methods for diagnosing a skin disorder or detecting a risk of developing a skin disorder in a human subject, comprising: detecting an alteration in a nucleic acid molecule encoding a CRNN protein obtained from the human subject, wherein the alteration encodes a loss-of-function CRNN protein or a CRNN protein truncated at a position corresponding to position 79 according to SEQ ID NO:8; and diagnosing the human subject with a skin disorder if the subject has one or more symptoms of a skin disorder, or diagnosing the human subject as at risk for developing a skin disorder if the subject does not have one or more symptoms of a skin disorder.

The present disclosure also provides methods for diagnosing a skin disorder or detecting a risk of developing a skin disorder in a human subject, comprising: detecting in a nucleic acid molecule obtained from the human subject any of the alterations in any of the CRNN nucleic acid molecules described herein; and diagnosing the human subject with a skin disorder if the subject has one or more symptoms of a skin disorder, or diagnosing the human subject as at risk for developing a skin disorder if the subject does not have one or more symptoms of a skin disorder. In some embodiments, the human subject is in need of such diagnosis. In some embodiments, the human subject may have relatives that have been diagnosed with a skin disorder.

Symptoms of skin disorders include, but are not limited to, psoriatic rash, formation of itchy, red, and dry patches in the skin, formation of itchy, dry scales in the skin, appearance of silvery-white scaly skin patches, inflammation of patches of skin, widespread inflammation or exfoliation of the skin, swelling and pain of the inflamed skin, appearance of pustules or papules in the skin, pitting of the nails of hands and toes, discoloration or whitening of the nails of hands and toes, thickening of the skin under the nails of hands and toes, loosening or crumbling of the nails of hands and toes, inflammation of the joints and surrounding tissues.

In some embodiments, the methods comprise detecting the presence of the variant CRNN genomic DNA, mRNA, or cDNA obtained from mRNA obtained from a biological sample obtained from the subject. It is understood that gene sequences within a population and mRNAs encoded by such genes can vary due to polymorphisms such as single nucleotide polymorphisms (SNPs). The sequences provided herein for the CRNN genomic DNA, mRNA, cDNA, and polypeptide are only exemplary sequences and other such sequences, including additional CRNN alleles are also possible.

In some embodiments, the detecting step comprises sequencing at least a portion of the nucleic acid molecule that encodes a loss-of-function CRNN protein or truncated CRNN protein. In some embodiments, the detecting step comprises sequencing at least a portion of the nucleic acid molecule that encodes a CRNN protein, wherein the sequenced nucleic acid molecule encodes an amino acid sequence which comprises the position corresponding to position 69 according to SEQ ID NO:8. Any of the nucleic acid molecules disclosed herein (e.g., genomic DNA, mRNA, or cDNA) can be sequenced. In some embodiments, the detecting step comprises sequencing the entire nucleic acid molecule.

In some embodiments, the detecting step comprises: amplifying at least a portion of the nucleic acid molecule that encodes a loss-of-function CRNN protein or truncated CRNN protein; labeling the nucleic acid molecule with a detectable label; contacting the labeled nucleic acid with a support comprising a probe, wherein the probe comprises a nucleic acid sequence which hybridizes under stringent conditions to a nucleic acid sequence encoding the loss-of-function CRNN protein or truncated CRNN protein; and detecting the detectable label. In some embodiments, the detecting step comprises: amplifying at least a portion of the nucleic acid molecule that encodes a CRNN protein, wherein the amplified nucleic acid molecule encodes an amino acid sequence which comprises the position corresponding to position 69 according to SEQ ID NO:8; labeling the nucleic acid molecule with a detectable label; contacting the labeled nucleic acid with a support comprising a probe, wherein the probe comprises a nucleic acid sequence which hybridizes under stringent conditions to a nucleic acid sequence encoding cysteine at the position corresponding to position at 69 according to SEQ ID NO:8; and detecting the detectable label. Any of the nucleic acid molecules disclosed herein can be amplified. For example, any of the genomic DNA, cDNA, or mRNA molecules disclosed herein can be amplified. In some embodiments, the nucleic acid molecule is mRNA and the method further comprises reverse-transcribing the mRNA into a cDNA prior to the amplifying step.

In some embodiments, the detecting step comprises: contacting the nucleic acid molecule that encodes a CRNN protein with a probe comprising a detectable label, wherein the probe comprises a nucleic acid sequence which hybridizes under stringent conditions to a nucleic acid sequence encoding a loss-of-function CRNN protein or a truncated CRNN protein, and detecting the detectable label. In some embodiments, the detecting step comprises: contacting the nucleic acid molecule that encodes a CRNN protein with a probe comprising a detectable label, wherein the probe comprises a nucleic acid sequence which hybridizes under stringent conditions to a nucleic acid sequence encoding an amino acid sequence which comprises a cysteine at the position corresponding to position 69 according to SEQ ID NO:8, and detecting the detectable label. In some embodiments, the nucleic acid molecule is present within a cell obtained from the human subject, such that the detection is according to an in situ hybridization technique.

In some embodiments, the detecting step comprises contacting the nucleic acid molecule that encodes a CRNN protein with an alteration-specific primer, and amplifying the nucleic acid molecule using alteration-specific PCR techniques. The alteration-specific primer may be any such primer described herein, and may be specific to variant CRNN proteins that encode a cysteine at the position corresponding to position 69 according to SEQ ID NO:8.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by detection of the presence and quantity of variant mRNA or cDNA in the biological sample.

The present disclosure also provides methods for identifying a human subject having a skin disorder or at risk for developing a skin disorder, wherein the method comprises detecting in a sample obtained from the subject the presence or absence of: a loss-of-function CRNN protein or a truncated CRNN protein; and/or a nucleic acid molecule encoding a loss-of-function CRNN protein or a truncated CRNN protein; wherein the presence of the loss-of-function CRNN protein or a truncated CRNN protein and/or the nucleic acid molecule encoding the loss-of-function CRNN protein or a truncated CRNN protein indicates that the subject has a skin disorder or a risk for developing a skin disorder.

The present disclosure also provides methods for identifying a human subject having a skin disorder or at risk for developing a skin disorder, wherein the method comprises detecting in a sample obtained from the subject the presence or absence of: a loss-of-function CRNN protein or a CRNN protein truncated at a position corresponding to position 79 according to SEQ ID NO:8; and/or a nucleic acid molecule encoding a loss-of-function CRNN protein or a CRNN protein truncated at a position corresponding to position 79 according to SEQ ID NO:8; wherein the presence of the loss-of-function CRNN protein or a CRNN protein and/or the nucleic acid molecule encoding the loss-of-function CRNN protein or a CRNN protein indicates that the subject has a skin disorder or a risk for developing a skin disorder.

The present disclosure also provides methods for identifying a human subject having a skin disorder or a risk for developing a skin disorder. The methods generally comprise detecting in a sample obtained from the subject the presence or absence of a variant CRNN protein; and/or the presence or absence of any of the nucleic acid molecules described herein encoding a variant CRNN protein. The presence of a loss-of-function CRNN protein or truncated CRNN protein, indicates that the subject has a skin disorder or a risk for developing a skin disorder. The presence of a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8, indicates that the subject has a skin disorder or a risk for developing a skin disorder. The method may be carried out in vitro, in situ, or in vivo.

The present disclosure also provides methods for identifying a human subject having a skin disorder or a risk for developing a skin disorder, wherein the method comprises detecting in a sample obtained from the subject the presence or absence of: a CRNN protein having a cysteine at the position corresponding to position 69 according to SEQ ID NO:8 and being truncated at the position corresponding to position 79 according to SEQ ID NO:8; and/or a nucleic acid molecule encoding a CRNN protein having a cysteine at the position corresponding to position 69 according to SEQ ID NO:8 and being truncated at the position corresponding to position 79 according to SEQ ID NO:8; wherein the presence of the loss-of-function CRNN protein or truncated CRNN protein and/or the nucleic acid molecule encoding the loss-of-function CRNN protein or truncated CRNN protein indicates that the subject has a skin disorder or a risk for developing a skin disorder. In some embodiments, the loss-of-function CRNN protein or truncated CRNN protein comprises a different amino acid compared to the wild type CRNN protein at any one of the positions corresponding to positions 69 to 76, 78, and 79 according to SEQ ID NO:8. In some embodiments, the loss-of-function CRNN protein or truncated CRNN protein comprises the amino acid sequence of SEQ ID NO:10 at the positions corresponding to positions 69 to 79 according to SEQ ID NO:8.

In some embodiments, the presence or absence of the loss-of-function CRNN protein or truncated CRNN protein in the sample is detected with an antibody which is specific for the loss-of-function CRNN protein or truncated CRNN protein. In some embodiments, the antibody which is specific for loss-of-function CRNN protein or truncated CRNN is specific for: i) cysteine at the position corresponding to position 69 according to SEQ ID NO:8; or ii) an epitope created in the CRNN protein because of a frameshift mutation which results in a cysteine at the position corresponding to position 69 according to SEQ ID NO:8. In some embodiments, the detection further comprises comparing the reaction of the antibody which is specific for loss-of-function CRNN protein or truncated CRNN with the reaction of an antibody that is specific for wild type CRNN. In some embodiments, the presence or absence of the loss-of-function CRNN protein or truncated CRNN protein in the sample is detected by an enzyme-linked immunosorbent assay (ELISA). In some embodiments, the presence or absence of the nucleic acid molecule encoding the loss-of-function CRNN protein or truncated CRNN protein in the sample is detected by determining whether there is a frameshift mutation in the nucleic acid molecule creating a codon encoding a cysteine at the position corresponding to position 69 according to SEQ ID NO:8. In some embodiments, the portion of the nucleic acid molecule sequenced comprises a plurality of positions encompassing the codon encoding the position corresponding to the position 69 according to SEQ ID NO:8.

In some embodiments of the method, the detecting step comprises sequencing at least a portion of the nucleic acid molecule that encodes a CRNN protein. In some embodiments of the method, the detecting step comprises sequencing at least a portion of the nucleic acid molecule that encodes a loss-of-function CRNN protein or truncated CRNN protein. The sequenced nucleic acid molecule may encode an amino acid sequence which comprises a position corresponding to position 69 according to SEQ ID NO:8. The presence of a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8. The detecting step may comprise sequencing the nucleic acid molecule encoding the entire CRNN protein.

In some embodiments of the method, the detecting step comprises amplifying at least a portion of the nucleic acid molecule that encodes a loss-of-function CRNN protein or truncated CRNN protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding the loss-of-function CRNN protein or truncated CRNN protein, and detecting the detectable label. In some embodiments of the method, the detecting step comprises amplifying at least a portion of the nucleic acid molecule that encodes a CRNN protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding a cysteine at the position corresponding to position 69 according to SEQ ID NO:8 (or a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8), and detecting the detectable label. The amplified nucleic acid molecule preferably encodes an amino acid sequence which comprises the position corresponding to position 69 according to SEQ ID NO:8. If the nucleic acid includes mRNA, the method may further comprise reverse-transcribing the mRNA into a cDNA prior to the amplifying step. In some embodiments, the determining step comprises contacting the nucleic acid molecule that encodes a CRNN protein with a probe comprising a detectable label and detecting the detectable label. The probe preferably comprises a nucleic acid sequence which specifically hybridizes, including, for example, under stringent conditions, to a nucleic acid sequence encoding an amino acid sequence which comprises a cysteine at the position corresponding to position at 69 according to SEQ ID NO:8 (or a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 79 according to SEQ ID NO:8). The nucleic acid molecule may be present within a cell obtained from the human subject.

In some embodiments, the detecting step comprises: amplifying at least a portion of the nucleic acid molecule that encodes a CRNN protein, wherein the amplified nucleic acid molecule encompasses the codon encoding the amino acid at the position corresponding to position 69 according to SEQ ID NO:8; labeling the amplified nucleic acid molecule with a detectable label; contacting the labeled nucleic acid molecule with a support comprising a probe, wherein the probe comprises a nucleic acid sequence which specifically hybridizes under stringent conditions to a nucleic acid sequence encompassing the codon encoding a cysteine at the position corresponding to position 69 according to SEQ ID NO:8; and detecting the detectable label.

In some embodiments, the detecting step comprises: contacting a nucleic acid molecule that encodes a CRNN protein with a probe comprising a detectable label, wherein the probe comprises a nucleic acid sequence which specifically hybridizes under stringent conditions to a nucleic acid sequence encompassing the codon encoding cysteine at the position corresponding to position 69 according to SEQ ID NO:8; and detecting the detectable label. In some embodiments, the human subject is identified as having a skin disorder or a risk for developing a skin disorder.

The present disclosure also provides methods for diagnosing a skin disorder or detecting a risk of developing a skin disorder in a human subject, comprising: detecting a loss-of-function CRNN protein or truncated CRNN protein obtained from the human subject; and diagnosing the human subject with a skin disorder if the subject has one or more symptoms of a skin disorder, or diagnosing the human subject as at risk for developing a skin disorder if the subject does not have one or more symptoms of a skin disorder. In some embodiments, the human subject is in need of such diagnosis. The present disclosure also provides methods for diagnosing a skin disorder or detecting a risk of developing a skin disorder in a human subject, comprising: detecting a variant CRNN protein, such as a protein comprising SEQ ID NO:8, obtained from the human subject; and diagnosing the human subject with a skin disorder if the subject has one or more symptoms of a skin disorder, or diagnosing the human subject as at risk for developing a skin disorder if the subject does not have one or more symptoms of a skin disorder. In some embodiments, the human subject is in need of such diagnosis. In some embodiments, the human subject may have relatives that have been diagnosed with a skin disorder.

The present disclosure also provides methods for diagnosing a skin disorder or detecting a risk of a skin disorder in a human subject, comprising: detecting a nucleic acid molecule encoding a variant CRNN protein obtained from the human subject, wherein the CRNN protein has a cysteine at the position corresponding to position 69 according to SEQ ID NO:8 and is truncated at a position corresponding to position 79 according to SEQ ID NO:8; and/or detecting a CRNN protein obtained from the human subject, wherein the CRNN protein has a cysteine at the position corresponding to position 69 according to SEQ ID NO:8 and is truncated at the position corresponding to position 79 according to SEQ ID NO:8; and diagnosing the human subject with a skin disorder if the subject has one or more symptoms of a skin disorder, or diagnosing the human subject as at risk for a skin disorder if the subject does not have one or more symptoms of a skin disorder. In some embodiments, the variant CRNN protein is a loss-of-function CRNN protein or truncated CRNN protein. In some embodiments, the variant CRNN protein comprises a different amino acid compared to the wild type CRNN protein at any one of the positions corresponding to positions 69 to 76, 78, and 79 according to SEQ ID NO:8. In some embodiments, the loss-of-function CRNN protein or truncated CRNN protein comprises the amino acid sequence of SEQ ID NO:10 at the positions corresponding to positions 69 to 79 according to SEQ ID NO:8. In some embodiments, the loss-of-function CRNN protein or truncated CRNN protein is detected with an antibody which is specific for loss-of-function CRNN protein or truncated CRNN. In some embodiments, the antibody which is specific for loss-of-function CRNN protein or truncated CRNN is specific for: i) cysteine at the position corresponding to position 69 according to SEQ ID NO:8; or ii) an epitope created in the CRNN protein because of a frameshift mutation which results in a cysteine at the position corresponding to position 69 according to SEQ ID NO:8. In some embodiments, the detection further comprises comparing the reaction of the antibody which is specific for loss-of-function CRNN protein or truncated CRNN with the reaction of an antibody that is specific for wild type CRNN. In some embodiments, the loss-of-function CRNN protein or truncated CRNN protein is detected by an enzyme-linked immunosorbent assay (ELISA). In some embodiments, the nucleic acid molecule encoding the loss-of-function CRNN protein or truncated CRNN protein is detected by detecting a frameshift mutation in the nucleic acid molecule creating a codon encoding a cysteine at the position corresponding to position 69 according to SEQ ID NO:8. In some embodiments, the portion of the nucleic acid molecule sequenced comprises a plurality of positions encompassing the codon encoding the position corresponding to the position 69 according to SEQ ID NO:8.

In some embodiments, the detecting step comprises: amplifying at least a portion of the nucleic acid molecule that encodes a CRNN protein, wherein the amplified nucleic acid molecule encompasses the codon encoding the amino acid at the position corresponding to position 69 according to SEQ ID NO:8; labeling the amplified nucleic acid molecule with a detectable label; contacting the labeled nucleic acid molecule with a support comprising a probe, wherein the probe comprises a nucleic acid sequence which specifically hybridizes under stringent conditions to a nucleic acid sequence encompassing the codon encoding a cysteine at the position corresponding to position 69 according to SEQ ID NO:8; and detecting the detectable label.

In some embodiments, the detecting step comprises: contacting the nucleic acid molecule that encodes a CRNN protein with a probe comprising a detectable label, wherein the probe comprises a nucleic acid sequence which specifically hybridizes under stringent conditions to a nucleic acid sequence encompassing the codon encoding cysteine at the position corresponding to position 69 according to SEQ ID NO:8; and detecting the detectable label.

In some embodiments, any of the methods described herein can further comprise treating the subject with an agent effective to treat a skin disorder. In some embodiments, the methods further comprise treating the subject with an agent effective to treat a skin disorder when the alteration is detected in the subject and the subject is diagnosed as having a skin disorder.

In some embodiments, the skin disorder is psoriasis, eczema, or atopic dermatitis. In some embodiments, the skin disorder is psoriasis. In some embodiments, the skin disorder is eczema. In some embodiments, the skin disorder is atopic dermatitis. In some embodiments, the psoriasis is psoriasis vulgaris, pustular psoriasis, or psoriatic arthritis.

In some embodiments, the agent effective to treat a skin disorder is or comprises a vitamin. In some embodiments, the vitamin is Vitamin A or Vitamin D. In some embodiments, the agent effective to treat a skin disorder is salicylic acid. In some embodiments, the agent effective to treat a skin disorder is eicosapentaenoic acid (EPA). In some embodiments, the agent effective to treat a skin disorder is a corticosteroid. In some embodiments, the agent effective to treat a skin disorder is psoralen. In some embodiments, the agent effective to treat a skin disorder is methotrexate. In some embodiments, the agent effective to treat a skin disorder is cyclosporine. In some embodiments, the agent effective to treat a skin disorder is an antibody, or at least the antigen binding domain thereof.

In some embodiments, the agent effective to treat a skin disorder is adalimumab) (Humira®), or at least the antigen binding domain thereof. In some embodiments, the agent effective to treat a skin disorder is brodalumab (Siliq®), or at least the antigen binding domain thereof. In some embodiments, the agent effective to treat a skin disorder is etanercept (Enbrel®), or at least the antigen binding domain thereof. In some embodiments, the agent effective to treat a skin disorder is ixekizumab (Taltz®), or at least the antigen binding domain thereof. In some embodiments, the agent effective to treat a skin disorder is secukinumab (Cosentyx®), or at least the antigen binding domain thereof. In some embodiments, the agent effective to treat a skin disorder is ustekinumab (Stelara®), or at least the antigen binding domain thereof.

Administration of the treatment agents can be by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The present disclosure also provides methods for treating a patient with a skin disorder therapeutic agent, wherein the patient is suffering from a skin disorder. The methods comprise determining whether or not a sample from the subject comprises any of the variant CRNN nucleic acid molecules described herein (e.g., nucleic acid molecules encoding a loss-of-function CRNN protein or truncated CRNN protein, nucleic acid molecules comprising a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8) or a variant CRNN protein truncated at a position corresponding to position 79 according to SEQ ID NO:8 and containing a cysteine at a position corresponding to position 69 according to SEQ ID NO:8. In some embodiments, the methods comprise determining whether or not a sample from the subject comprises a nucleic acid molecule encoding a loss-of-function CRNN protein or a truncated CRNN protein. In some embodiments, the methods comprise determining whether or not a sample from the subject comprises a nucleic acid molecule comprising a nucleic acid sequence having a thymine at a position corresponding to position 3375 according to SEQ ID NO:2. In some embodiments, the methods comprise determining whether or not a sample from the subject comprises a nucleic acid molecule comprising a nucleic acid sequence having a uracil at a position corresponding to position 205 according to SEQ ID NO:4. In some embodiments, the methods comprise determining whether or not a sample from the subject comprises a nucleic acid molecule comprising a nucleic acid sequence having a thymine at a position corresponding to position 205 according to SEQ ID NO:6. In some embodiments, the methods comprise determining whether or not a sample from the subject comprises a variant CRNN protein truncated at a position corresponding to position 79 according to SEQ ID NO:8 and containing a cysteine at a position corresponding to position 69 according to SEQ ID NO:8.

In some embodiments, this determination is carried out by obtaining or having obtained a biological sample from the patient. In some embodiments, the methods further comprise performing or having performed a genotyping assay on the biological sample to determine if the patient has any of the variant CRNN nucleic acid molecules described herein (e.g., nucleic acid molecules encoding a loss-of-function CRNN protein or truncated CRNN protein, nucleic acid molecules comprising a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8). In some embodiments, the methods further comprise performing or having performed a genotyping assay on the biological sample to determine if the patient has a nucleic acid molecule encoding a loss-of-function CRNN protein or a truncated CRNN protein. In some embodiments, the methods further comprise performing or having performed a genotyping assay on the biological sample to determine if the patient has a nucleic acid molecule comprising a nucleic acid sequence having a thymine at a position corresponding to position 3375 according to SEQ ID NO:2. In some embodiments, the methods further comprise performing or having performed a genotyping assay on the biological sample to determine if the patient has a nucleic acid molecule comprising a nucleic acid sequence having a uracil at a position corresponding to position 205 according to SEQ ID NO:4. In some embodiments, the methods further comprise performing or having performed a genotyping assay on the biological sample to determine if the patient has a nucleic acid molecule comprising a nucleic acid sequence having a thymine at a position corresponding to position 205 according to SEQ ID NO:6. In some embodiments, the methods further comprise performing or having performed an assay on the biological sample to determine if the patient has a variant CRNN protein truncated at a position corresponding to position 79 according to SEQ ID NO:8 and containing a cysteine at a position corresponding to position 69 according to SEQ ID NO:8.

In some embodiments, when the patient has any of the variant CRNN nucleic acid molecules described herein (e.g., nucleic acid molecules encoding a loss-of-function CRNN protein or truncated CRNN protein, nucleic acid molecules comprising a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8), then the method further comprises administering an agent effective to treat a skin disorder to the patient. In some embodiments, when the patient has a nucleic acid molecule encoding a loss-of-function CRNN protein or a truncated CRNN protein, then the method further comprises administering an agent effective to treat a skin disorder to the patient. In some embodiments, when the patient has a nucleic acid molecule comprising a nucleic acid sequence having a thymine at a position corresponding to position 3375 according to SEQ ID NO:2, then the method further comprises administering an agent effective to treat a skin disorder to the patient. In some embodiments, when the patient has a nucleic acid molecule comprising a nucleic acid sequence having a uracil at a position corresponding to position 205 according to SEQ ID NO:4, then the method further comprises administering an agent effective to treat a skin disorder to the patient. In some embodiments, when the patient has a nucleic acid molecule comprising a nucleic acid sequence having a thymine at a position corresponding to position 205 according to SEQ ID NO:6, then the method further comprises administering an agent effective to treat a skin disorder to the patient. In some embodiments, when the patient has a variant CRNN protein truncated at a position corresponding to position 79 according to SEQ ID NO:8 and containing a cysteine at a position corresponding to position 69 according to SEQ ID NO:8, then the method further comprises administering an agent effective to treat a skin disorder to the patient.

The present disclosure also provides treatment agents (such as any of those described herein) for use in the manufacture of a medicament for the treatment of a skin disorder in a human subject having any of the variant CRNN nucleic acid molecules described herein (e.g., nucleic acid molecules encoding a loss-of-function CRNN protein or truncated CRNN protein, nucleic acid molecules comprising a nucleic acid sequence having a thymine at a position corresponding to position 3375 according to SEQ ID NO:2 (e.g., the genomic DNA), or a uracil at a position corresponding to position 205 according to SEQ ID NO:4 (e.g., the mRNA), or a thymine at a position corresponding to position 205 according to SEQ ID NO:6 (e.g., the cDNA), each resulting in a variant CRNN protein truncated at a position corresponding to position 79 according to SEQ ID NO:8 and containing a cysteine at a position corresponding to position 69 according to SEQ ID NO:8) or a variant CRNN protein truncated at a position corresponding to position 79 according to SEQ ID NO:8 and containing a cysteine at a position corresponding to position 69 according to SEQ ID NO:8. In some embodiments, the human subject has been tested positive for the loss-of-function CRNN protein or truncated CRNN protein and/or for a nucleic acid molecule encoding the loss-of-function CRNN protein or truncated CRNN protein. In some embodiments, the treatment comprises the step of determining whether or not the human subject has the loss-of-function CRNN protein or truncated CRNN protein and/or a nucleic acid molecule encoding the loss-of-function CRNN protein or truncated CRNN protein. In some embodiments, the human subject has been identified as having a skin disorder or as having a risk for developing a skin disorder by using the any of the methods described herein. In some embodiments, the loss-of-function CRNN protein or truncated CRNN protein comprises a different amino acid compared to the wild type CRNN protein at any of positions corresponding to positions 69 to 76, 78, and 79 according to SEQ ID NO:8. In some embodiments, the loss-of-function CRNN protein or truncated CRNN protein comprises a cysteine at a position corresponding to position 69 according to SEQ ID NO:8. In some embodiments, the loss-of-function CRNN protein or truncated CRNN protein comprises the amino acid sequence of SEQ ID NO:8, or an amino acid sequence that has at least 90% sequence identity to SEQ ID NO:8, and comprises cysteine at a position corresponding to position 69 according to SEQ ID NO:8. In some embodiments, the agent effective to treat a skin disorder is or comprises a vitamin. In some embodiments, the vitamin is Vitamin A or Vitamin D. In some embodiments, the agent effective to treat a skin disorder is salicylic acid. In some embodiments, the agent effective to treat a skin disorder is eicosapentaenoic acid (EPA). In some embodiments, the agent effective to treat a skin disorder is a corticosteroid. In some embodiments, the agent effective to treat a skin disorder is psoralen. In some embodiments, the agent effective to treat a skin disorder is methotrexate. In some embodiments, the agent effective to treat a skin disorder is cyclosporine. In some embodiments, the agent effective to treat a skin disorder is an antibody, or at least the antigen binding domain thereof. In some embodiments, the agent effective to treat a skin disorder is adalimumab (Humira®), or at least the antigen binding domain thereof. In some embodiments, the agent effective to treat a skin disorder is brodalumab (Siliq®), or at least the antigen binding domain thereof. In some embodiments, the agent effective to treat a skin disorder is etanercept (Enbrel®), or at least the antigen binding domain thereof. In some embodiments, the agent effective to treat a skin disorder is ixekizumab (Taltz®), or at least the antigen binding domain thereof. In some embodiments, the agent effective to treat a skin disorder is secukinumab (Cosentyx®), or at least the antigen binding domain thereof. In some embodiments, the agent effective to treat a skin disorder is ustekinumab (Stelara®), or at least the antigen binding domain thereof.

The present disclosure also provides skin disorder treatment agents for use in the treatment of a skin disorder in a human subject having a loss-of-function CRNN protein or CRNN protein truncated at a position corresponding to position 79 according to SEQ ID NO:8. In some embodiments, the human subject has been tested positive for the loss-of-function CRNN protein or truncated CRNN protein and/or for a nucleic acid molecule encoding the loss-of-function CRNN protein or truncated CRNN protein. In some embodiments, the treatment comprises the step of determining whether or not the human subject has the loss-of-function CRNN protein or truncated CRNN protein and/or a nucleic acid molecule encoding the loss-of-function CRNN protein or truncated CRNN protein. In some embodiments, the human subject has been identified as having a skin disorder or as having a risk for developing a skin disorder by using any of the methods as defined herein. In some embodiments, the loss-of-function CRNN protein or truncated CRNN protein comprises a different amino acid compared to the wild type CRNN protein at any one of the positions corresponding to positions 69 to 76, 78, and 79 according to SEQ ID NO:8. In some embodiments, the loss-of-function CRNN protein or truncated CRNN protein comprises a cysteine at a position corresponding to position 69 according to SEQ ID NO:8. In some embodiments, the loss-of-function CRNN protein or truncated CRNN protein comprises the amino acid sequence of SEQ ID NO:10 at the positions corresponding to positions 69 to 79 according to SEQ ID NO:8. In some embodiments, the loss-of-function CRNN protein or truncated CRNN protein comprises the amino acid sequence of SEQ ID NO:8, or an amino acid sequence that has at least 90% sequence identity to SEQ ID NO:8 and comprises a cysteine at a position corresponding to position 69 according to SEQ ID NO:8. In some embodiments, the agent effective to treat a skin disorder is or comprises a vitamin. In some embodiments, the vitamin is Vitamin A or Vitamin D. In some embodiments, the agent effective to treat a skin disorder is salicylic acid. In some embodiments, the agent effective to treat a skin disorder is eicosapentaenoic acid (EPA). In some embodiments, the agent effective to treat a skin disorder is a corticosteroid. In some embodiments, the agent effective to treat a skin disorder is psoralen. In some embodiments, the agent effective to treat a skin disorder is methotrexate. In some embodiments, the agent effective to treat a skin disorder is cyclosporine. In some embodiments, the agent effective to treat a skin disorder is an antibody, or at least the antigen binding domain thereof. In some embodiments, the agent effective to treat a skin disorder is adalimumab (Humira®), or at least the antigen binding domain thereof. In some embodiments, the agent effective to treat a skin disorder is brodalumab (Siliq®), or at least the antigen binding domain thereof. In some embodiments, the agent effective to treat a skin disorder is etanercept (Enbrel®), or at least the antigen binding domain thereof. In some embodiments, the agent effective to treat a skin disorder is ixekizumab (Taltz®), or at least the antigen binding domain thereof. In some embodiments, the agent effective to treat a skin disorder is secukinumab (Cosentyx®), or at least the antigen binding domain thereof. In some embodiments, the agent effective to treat a skin disorder is ustekinumab (Stelara®), or at least the antigen binding domain thereof.

The present disclosure also provides uses of any of the variant CRNN genomic DNA, mRNA, cDNA, polypeptides, and hybridizing nucleic acid molecules disclosed herein in the diagnosis of a skin disorder or diagnosing the risk of developing a skin disorder.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Patient Recruitment and Phenotyping

Whole exome sequencing and trio-based variant analysis was performed on a 8-member family segregating psoriasis in a dominant inheritance pattern in 6 affected individuals and 2 unaffected individuals (see, FIG. 1) from a collaboration between the Regeneron Genetics Center (RGC) and the University of Utah. A novel, not previously observed insertion mutation (c.203_204 insT; p.V69Cfs*12) was identified in the CRNN (Cornulin) gene segregating in a family with psoriasis.

Example 2: Genomic Samples

Genomic DNA was extracted from peripheral blood samples and transferred to the Regeneron Genetics Center (RGC) for whole exome sequencing, and stored in automated biobanks at −80° C. Fluorescence-based quantification was performed to ensure appropriate DNA quantity and quality for sequencing purposes.

1 μg of DNA was sheared to an average fragment length of 150 base pairs (Covaris LE220) and prepared for exome capture with a custom reagent kit from Kapa Biosystems. Samples were captured using the NimbleGen SeqCap VCRome 2.1 or the Integrated DNA Technologies xGen exome target designs. Samples were barcoded, pooled, and multiplexed for sequenced using 75 bp paired-end sequencing on an Illumina HiSeq 2500 with v4 chemistry. Captured fragments were sequenced to achieve a minimum of 85% of the target bases covered at 20× or greater coverage. Following sequencing, data was processed using a cloud-based pipeline developed at the RGC that uses DNAnexus and AWS to run standard tools for sample-level data production and analysis. Briefly, sequence data were generated and de-multiplexed using Illumina's CASAVA software. Sequence reads were mapped and aligned to the GRCh37/hg19 human genome reference assembly using BWA-mem. After alignment, duplicate reads were marked and flagged using Picard tools and indels were realigned using GATK to improve variant call quality. SNP and INDEL variants and genotypes were called using GATK's HaplotypeCaller and Variant Quality Score Recalibration (VQSR) from GATK was applied to annotate the overall variant quality scores. Sequencing and data quality metric statistics were captured for each sample to evaluate capture performance, alignment performance, and variant calling.

Example 3: Genomic Data Analyses

Standard quality-control filters for minimum read depth (>10), genotype quality (>30), and allelic balance (>20%) were applied to called variants. Passing variants were classified and annotated based on their potential functional effects (whether synonymous, nonsynonymous, splicing, frameshift, or nonframeshift variants) using an RGC developed annotation and analysis pipeline. Familial relationships were verified through identity by descent derived metrics from genetic data to infer relatedness and relationships in the cohort using PRIMUS (Staples et al., Amer. J. Human Genet., 2014, 95, 553-564) and cross-referencing with the reported pedigree for this family.

Pedigree-based variant analyses and segregation were performed to identify candidate disease genes under an autosomal dominant inheritance pattern given the reported family history. Shared variants between all the affected individuals were subsequently annotated and filtered by their observed frequencies in population control databases such as dbSNP, the 1000 Genomes Project, the NHLBI Exome Sequencing Project, the Exome Aggregation Consortium Database (ExAc), and internal RGC databases to filter out common polymorphisms and high frequency, likely benign variants. Algorithms for bioinformatic prediction of functional effects of variants, such as LRT, Poly-phen2, SIFT, CADD, and Mutation Taster, along with conservation scores based on multiple species alignments (i.e. GERP, PhastCons, PhyloP) were incorporated as part of the annotation process of variants and used to inform on the potential deleteriousness of identified candidate variants.

A rare, frameshifting 1 base pair insertion variant predicted to result in downstream truncation was identified in the CRNN gene (CRNN: c.203_204 insT; p.V69Cfs*12) segregating with the psoriasis disease phenotype and not present in the two unaffected individuals from the family.

Referring to FIG. 1 (panels A, B, and C), identification of a truncating variant in the CRNN gene with dominant segregation in a family with Psoriasis is shown. Panel A shows a table describing the truncating variant in CRNN at c.203_204 insT; p.V69Cfs*12 with autosomal dominant inheritance; the variant site affects and changes a conserved Valine residue at position 69 to Cysteine and produces an early truncation of the protein and predicted to be damaging to protein function, likely leading to a loss of function of CRNN. The variant identified in this family is rare and has not been previously observed in publicly available databases including Thousand Genomes Project (TGP), Exome Sequence Project (ESP), or the Exome Aggregation Consortium (ExAC) databases. Panel B shows the pedigree of the family studied; filled symbols indicate Psoriasis-affected individuals, unfilled symbols indicate unaffected individuals; circles denote females and squares denote males. Panel C shows the location of the rare variant resulting in a premature truncation of the protein, likely leading to nonsense mediated decay and loss of function of one copy of CRNN. Panel D shows the conservation in multiple species of the Valine residue at position 69 of the CRNN protein.

Example 4: Detection

The presence of a certain genetic variant in a subject can indicate that the subject has an increased risk of having or developing a skin disorder such as psoriasis, eczema or atopic dermatitis. A sample, such as a blood sample, can be obtained from a subject. Nucleic acids can be isolated from the sample using common nucleic acid extraction kits. After isolating the nucleic acid from the sample obtained from the subject, the nucleic acid is sequenced to determine if there is a genetic variant present. The sequence of the nucleic acid can be compared to a control sequence (wild type sequence). Finding a difference between the nucleic acid obtained from the sample obtained from the subject and the control sequence indicates the presence of a genetic variant. These steps can be performed as described in the examples above and throughout the present disclosure. The presence of one or more genetic variants is indicative of the subject's increased risk for having or developing a skin disorder such as psoriasis, eczema, or atopic dermatitis.

What is claimed:

1. A cDNA comprising a nucleic acid sequence encoding a cornulin protein truncated at a position corresponding to position 79 according to SEQ ID NO:8.

2. The cDNA according to claim 1, wherein the cornulin protein comprises cysteine at the position corresponding to position 69 according to SEQ ID NO:8.

3. The cDNA according to claim 2, wherein the cornulin protein comprises a different amino acid compared to the wild type cornulin protein at any one of the positions corresponding to positions 69 to 76, 78, and 79 according to SEQ ID NO:8.

4. The cDNA according to claim 2, wherein the cornulin protein comprises the amino acid sequence of SEQ ID NO:10 at the positions corresponding to positions 69 to 79 according to SEQ ID NO:8.

5. The cDNA according to claim 1, wherein the cornulin protein comprises the amino acid sequence according to SEQ ID NO:8, or an amino acid sequence that has at least 90% sequence identity to SEQ ID NO:8 and comprises a cysteine at a position corresponding to position 69 according to SEQ ID NO:8.

6. The cDNA according to claim 1, wherein the cornulin protein comprises the amino acid sequence according to SEQ ID NO:10.

7. The cDNA according to claim 1, wherein the cDNA comprises a thymine at a position corresponding to position 205 according to SEQ ID NO:6.

8. The cDNA according to claim 7, wherein the cDNA comprises the codons ACT and TGT at positions corresponding to positions 202 to 204 and 205 to 207, respectively, according to SEQ ID NO:6.

9. The cDNA according to claim 7, wherein the cDNA comprises SEQ ID NO:6.

10. A vector comprising the cDNA according to claim 1.

11. A host cell comprising the cDNA according to claim 1.

12. A host cell comprising the vector according to claim 10.

13. The host cell according to claim 11, wherein the cDNA is operably linked to a promoter active in the host cell.

14. The host cell according to claim 11, wherein the host cell is a mammalian cell.

* * * * *

SEQUENCE LISTING

<160> NUMBER OF SEQ ID NOS: 18

<210> SEQ ID NO 1
<211> LENGTH: 5009
<212> TYPE: DNA
<213> ORGANISM: homo sapien

<400> SEQUENCE: 1

```
cacttaacag ccacttgttt catcccacct gggcattagg taagtcccct cataagaaac      60
ctctttctca ttctcagtgt cttggtgatc tgagctcata aaactggggc agtcaggtat     120
ggactatgca tccttcagag ctagctgtga gcactgggca aaccaacgct accgttggga     180
aacatgctct cctgaagcaa tcaggctttc tcctcctccc tgaggctggc ctgggagcag     240
ctcctctcac tgggaaactg tgtgggcagc ggctatgggg ccacccatgt gccttcctgg     300
atcagcaaag gtttctttt tctaaggctc tggaagcttc tttgcagtgc tgagagtcta     360
tgggatcaga atcagtttac ttatgccaac ctagacaata agatcaaact gtgtcatgga     420 tgaagggtt tacatgattc ccctctccta caccagggtg atatttaggc aaaatatgtg     480 tagattttc taaggaatct aaaatgtaac taaaaggtca tcttattatt ttattatcta     540
aaggtcagtg gttaaagtct gctacatggt tttaaaaaaa agaaagatat ttttcatcta     600
tgttgaggaa aacatcccca gtttttacc ttgatgaaaa gtttgcctga aattgttggt     660
taccaggtcc tagaaagggt ttctcctgaa cagcccacct tttgctatga cttactgagt     720
cctcatggcc acactaatct gcttttcta gaactcaagt ctccttcctt cctttttct     780 cttttcttctc ctacctatat ctgcctcgtc ccatcctctc tctggctttc cagctgctac     840
aggctccatc tccccttgca tttgagactt gtcatcttg ataccatctc ctcctttggg     900
tctctccaag gcttctgctt aatgaatctt caagtctctt ttccttttgc tcatgcaacc     960
aaacccaggc ctcacctcaa cctacctcta gatttctggc taatgaaaaa gaaaagcttt    1020 cccttgatt aggaaccaac tcataggtca ccagaaatct gggcctgatg gagccacgtg    1080
cctgttgggc aagctgactt ctctgataag tctcagggct gtggacagag gcgacatgca    1140
gagaaacttg gaccctcaga actggaaggc ctcccaccca aagaaggttc cccctcctg    1200 agcattccca gcaggtggta gcccagtttc ttcccacttt cccaaaaaaa acaagaaggg    1260
```

```
agggctgtgt ccctggaatt tctgcttggc tcccatccaa gacagggggtt gactcacaga    1320 tgtatttact tccttttggc gttcccgatg ggaccctaac acccttgtga taaataaata    1380
aatcctgtcc acagggtaca ttctagaaag cccattgcat ttgggttaag gaaaaatgga    1440
tcctaggatt tcttggctcc ttaaaaattg tgtggcctaa cttctctgag cctgtttcct    1500
cacctataaa aaaagtggaa aataataagg attagaagag atgatgtaca ggaaagtgat    1560
tatataggtg tacaaaaatt atatgtgtgt atatgtatat aatagcataa taattatatt    1620
taataaggag cacttaatat aagccaggca tctgccaagt gcttttttatg aattatgtct    1680 ttaaatcttc acaataatcc cacagagtac taatatcacc ttcaattaca atgagtagta    1740
aactgaggca tggagaggca aagcaacttg tcccagctca catcatactt aagtggtggg    1800
gccagcattt aatcctgact caggaacctg cctccatcct gtgtgctcct ccttcccata    1860
cataagatgc attatgtagg aaaggacaaa ggaagactaa aaacagagct gaacgtgcaa    1920
ggaaagacct agcagcagac gtgctataaa ggaaatagct gaggttgatt atggagcctc    1980
caagggaact tttcatcttt tccaggttga cttcaaagat gcctcagtta ctgcaaaaca    2040
ttaatgggat catcgaggcc ttcaggcgct atgcaaggac ggagggcaac tgcacagcgc    2100
tcacccgagg ggagctgaaa agactcttgg agcaagagtt tgccgatgtg attgtggtac    2160
ggtgtgctga ccgggtgga gaggggacat agcaggagag tgaaacctgg tttgcctgca    2220
gaggccttga cctggggaat ttgaggaggc agcagctaaa cccaggcctg ccgggacaga    2280
tggcagctgt gcaggcagaa aaaaaggtga agaaccaga gatggtcatg ggagttggca    2340
agtcctggct cttttagatta aaaccttggt tttaattaat tctaacttaa agacaaggta    2400
aaagggctct aaaaggacaa ctcagacagg agcagagcct tggaatattt caaaatgaaa    2460
ataattgctg ctttctgccg cctcttaaat ttgatacagt aaatatttcc cacgtctatc    2520
tgaaatgtaa tcatccattc atagacattc attagaagca tagctctggg cttgcacgaa    2580
gcagttactc aaaaatatta gcagactgat cacatcagaa atgaaatttt gaagagcagg    2640
ttgttaatag ctaggggaga ctttggagcc tcaccccacc ccacctggca aaccagaacc    2700
aaggccttga tgcactttcc tgtctttggt ttgcatctaa agcaaccagg atgatgatgg    2760
ccttagggac aaggacatat gggcacagaa ggatgctgca tccacatgct cagggcagcg    2820
ctgcaggggc ccactgcttc cctccctctt tatcatgggg aaacatctgg gcctcaatga    2880
ggagcgcaca gaattcccat ggggctgtgt tcccaacctg ctgctctttg tgctgggcct    2940
gctgaagaga ctaaggcctc agtgccaggg gcaaggtgcc aagggcagcc cagacagtca    3000
acttgagagc ccaaacagtt gcattgtgaa ttcaataatt tattaactct tcaataaatc    3060
tttatctaat tttcctgtag cccagaaatt gtgccaaata gaggctacca aacaaaaaat    3120
gctctctaca cttgagggag agagacggga ctaaaaaaaa ataaaggcaa ttaagtcttg    3180
ctgctgctct agccgtatgt gtgtgtagtg tgggtctga ggcaggggaa gctggcagca    3240
gattggaagg gacctgccca tgtcctcctc aggggaggga tgctgactcc acctcatctt    3300
ctcctcagaa accccacgat ccagcaactg tggatgaggt cctgcgtctg ctggatgaag    3360
accacacagg gactgtggaa ttcaaggaat tcctggtctt agtgtttaaa gttgcccagg    3420
cctgtttcaa gacactgagc gagagtgctg agggagcctg cggctctcaa gagtctggaa    3480
gcctccactc tggggcctcg caggagctgg gcgaaggaca gagaagtggc actgaagtgg    3540
gaagggcggg gaaagggcag cattatgagg ggagcagcca cagacagagc cagcagggtt    3600
```

```
ccagagggca gaacaggcct ggggttcaga cccagggtca ggccactggc tctgcgtggg    3660
tcagcagcta tgacaggcaa gctgagtccc agagccagga agaataagcc ccgcagatac   3720
aactctctgg gcagacagag cagacccaga aagctggaga aggcaagagg aatcagacaa   3780
cagagatgag gccagagaga cagccacaga ccagggaaca ggacagagcc caccagacag   3840
gtgagactgt gactggatct ggaactcaga cccaggcagg tgccacccag actgtggagc   3900
aggacagcag ccaccagaca ggaagaacca gcaagcagac acaggaggcc accaatgacc   3960
agaacagagg gactgagacc cacggtcaag gcaggagcca gaccagccag gctgtgacag   4020
gaggacatgc tcagatacag gcagggacac acacccagac acccacccag accgtggagc   4080
aggacagcag ccaccagaca ggaagcacca gcacccagac acaggagtcc accaatggcc   4140
agaacagagg gactgagatc cacggtcaag gcaggagcca gaccagccag gctgtgacag   4200
gaggacacac tcagatacag gcagggtcac acaccgagac tgtggagcag gacagaagcc   4260
aaactgtaag ccacggaggg gctagagaac agggacagac ccagacgcag ccaggcagtg   4320
gtcaaagatg gatgcaagtg agcaaccctg aggcaggaga gacagtaccg ggaggacagg   4380
cccagactgg ggcaagcact gagtcaggaa ggcaggagtg gagcagcact cacccaaggc   4440
gctgtgtgac agaagggcag ggagacagac agccacagt ggttggtgag gaatgggttg    4500
atgaccactc aagggagaca gtgatcctca ggctggacca gggcaacttg cataccagtg   4560
tttcctcagc acagggccag gatgcagccc agtcagaaga gaagcgaggc atcacagcta   4620
gagagctgta ttcctacttg agaagcacca agccatgact tccccgactc caatgtccag   4680
tactggaaga agacagctgg agagagtttg gcttgtcctg catggccaat ccagtgggtg   4740
catccctgga catcagctct tcattatgca gcttcccttt taggtctttc tcaatgagat   4800
aatttctgca aggagctttc tatcctgaac tcttctttct tacctgcttt gcggtgcaga   4860
ccctctcagg agcaggaaga ctcagagcaa gtcacccctt tgtactgaat tgtcctcatc   4920
ttgtgggggg tttcaggact attttttatct ctgacatctc tctattgccc catctaccct   4980
aatgcatcaa taaaacctta agccgctgg                                     5009
```

<210> SEQ ID NO 2
<211> LENGTH: 5010
<212> TYPE: DNA
<213> ORGANISM: homo sapien

<400> SEQUENCE: 2

```
cacttaacag ccacttgttt catcccacct gggcattagg taagtcccct cataagaaac     60
ctctttctca ttctcagtgt cttggtgatc tgagctcata aaactggggc agtcaggtat    120
ggactatgca tccttcagag ctagctgtga gcactgggca aaccaacgct accgttggga    180
aacatgctct cctgaagcaa tcaggctttc tcctcctccc tgaggctggc ctgggagcag    240
ctcctctcac tgggaaactg tgtgggcagc ggctatgggg ccacccatgt gccttcctgg    300
atcagcaaag gtttcttttt tctaaggctc tggaagcttc tttgcagtgc tgagagtcta    360
tgggatcaga atcagtttac ttatgccaac ctagacaata agatcaaact gtgtcatgga    420
tgaagggggtt tacatgattc ccctctccta caccagggtg atatttaggc aaaatatgtg    480
tagattttc taaggaatct aaaatgtaac taaaaggtca tcttattatt ttattatcta     540
aaggtcagtg gttaaagtct gctacatggt tttaaaaaaa agaaagatat ttttcatcta    600
tgttgaggaa aacatcccca gtttttttacc ttgatgaaaa gtttgcctga aattgttggt   660
taccaggtcc tagaaagggt ttctcctgaa cagcccacct tttgctatga cttactgagt    720
```

-continued

```
cctcatggcc acactaatct gcttttcta gaactcaagt ctccttcctt cctttttct       780 ctttcttctc ctacctatat ctgcctcgtc ccatcctctc tctggctttc cagctgctac     840
aggctccatc tccccttgca tttgagactt gtcatctttg ataccatctc ctcctttggg    900
tctctccaag gcttctgctt aatgaatctt caagtctctt ttccttttgc tcatgcaacc    960
aaacccaggc ctcacctcaa cctacctcta gatttctggc taatgaaaaa gaaaagcttt   1020 cccttttgatt aggaaccaac tcataggtca ccagaaatct gggcctgatg gagccacgtg  1080
cctgttgggc aagctgactt ctctgataag tctcagggct gtggacagag gcgacatgca   1140
gagaaacttg gaccctcaga actggaaggc ctcccaccca agaaggttc ccccctcctg    1200 agcattccca gcaggtggta gcccagtttc ttcccacttt cccaaaaaaa acaagaaggg   1260
agggctgtgt ccctggaatt tctgcttggc tcccatccaa gacaggggtt gactcacaga   1320
tgtatttact tcctttggc gttcccgatg ggaccctaac acccttgtga taaataaata    1380
aatcctgtcc acagggtaca ttctagaaag cccattgcat ttgggttaag gaaaaatgga   1440
tcctaggatt tcttggctcc ttaaaaattg tgtggcctaa cttctctgag cctgtttcct   1500
cacctataaa aaaagtggaa ataataagg attagaagag atgatgtaca ggaaagtgat    1560
tatataggtg tacaaaaatt atatgtgtgt atatgtatat aatagcataa taattatatt  1620
taataaggag cacttaatat aagccaggca tctgccaagt gcttttatg aattatgtct    1680 ttaaatcttc acaataatcc cacagagtac taatatcacc ttcaattaca atgagtagta   1740
aactgaggca tggagaggca aagcaacttg tcccagctca catcatactt aagtggtggg   1800
gccagcattt aatcctgact caggaacctg cctccatcct gtgtgctcct ccttcccata   1860
cataagatgc attatgtagg aaaggacaaa ggaagactaa aaacagagct gaacgtgcaa   1920
ggaaagacct agcagcagac gtgctataaa ggaaatagct gaggttgatt atggagcctc   1980
caagggaact tttcatcttt tccaggttga cttcaaagat gcctcagtta ctgcaaaaca   2040
ttaatgggat catcgaggcc ttcaggcgct atgcaaggac ggagggcaac tgcacagcgc   2100
tcacccgagg ggagctgaaa agactcttgg agcaagagtt tgccgatgtg attgtggtac   2160
ggtgtgctga gccgggtgga gagggacat agcaggagag tgaaacctgg tttgcctgca    2220
gaggccttga cctggggaat ttgaggaggc agcagctaaa cccaggcctg ccgggacaga   2280
tggcagctgt gcaggcagaa aaaaaggtga agaaccaga gatggtcatg ggagttggca    2340
agtcctggct ctttagatta aaaccttggt tttaattaat tctaacttaa agacaaggta   2400
aaagggctct aaaaggacaa ctcagacagg agcagagcct tggaatattt caaaatgaaa   2460
ataattgctg ctttctgccg cctcttaaat ttgatacagt aaatatttcc cacgtctatc   2520
tgaaatgtaa tcatccattc atagacattc attagaagca tagctctggg cttgcacgaa   2580
gcagttactc aaaaatatta gcagactgat cacatcagaa atgaaatttt gaagagcagg   2640
ttgttaatag ctaggggaga ctttggagcc tcaccccacc ccacctggca aaccagaacc   2700
aaggccttga tgcactttcc tgtctttggt ttgcatctaa agcaaccagg atgatgatgg   2760
ccttagggac aaggacatat gggcacagaa ggatgctgca tccacatgct cagggcagcg   2820 ctgcagggggc ccactgcttc cctccctctt tatcatgggg aaacatctgg gcctcaatga  2880
ggagcgcaca gaattcccat ggggctgtgt tcccaacctg ctgctctttg tgctgggcct   2940
gctgaagaga ctaaggcctc agtgccaggg gcaaggtgcc aagggcagcc cagacagtca   3000
acttgagagc ccaaacagtt gcattgtgaa ttcaataatt tattaactct tcaataaatc   3060
```

| | |
|---|---|
| tttatctaat tttcctgtag cccagaaatt gtgccaaata gaggctacca aacaaaaaat | 3120 |
| gctctctaca cttgagggag agagacggga ctaaaaaaaa ataaaggcaa ttaagtcttg | 3180 |
| ctgctgctct agccgtatgt gtgtgtagtg tggggtctga ggcagggaa gctggcagca | 3240 |
| gattggaagg gacctgccca tgtcctcctc aggggaggga tgctgactcc acctcatctt | 3300 |
| ctcctcagaa accccacgat ccagcaactg tggatgaggt cctgcgtctg ctggatgaag | 3360 |
| accacacagg gacttgtgga attcaaggaa ttcctggtct tagtgtttaa agttgcccag | 3420 |
| gcctgtttca agacactgag cgagagtgct gagggagcct gcggctctca agagtctgga | 3480 |
| agcctccact ctggggcctc gcaggagctg ggcgaaggac agagaagtgg cactgaagtg | 3540 |
| ggaagggcgg ggaagggca gcattatgag gggagcagcc acagacagag ccagcagggt | 3600 |
| tccagagggc agaacaggcc tggggttcag acccagggtc aggccactgg ctctgcgtgg | 3660 |
| gtcagcagct atgacaggca agctgagtcc cagagccagg aaagaataag cccgcagata | 3720 |
| caactctctg ggcagacaga gcagacccag aaagctggag aaggcaagag gaatcagaca | 3780 |
| acagagatga ggccagagag acagccacag accagggaac aggacagagc ccaccagaca | 3840 |
| ggtgagactg tgactggatc tggaactcag acccaggcag gtgccaccca gactgtggag | 3900 |
| caggacagca gccaccagac aggaagaacc agcaagcaga cacaggaggc caccaatgac | 3960 |
| cagaacagag ggactgagac ccacggtcaa ggcaggagcc agaccagcca ggctgtgaca | 4020 |
| ggaggacatg ctcagataca ggcagggaca cacacccaga cacccaccca gaccgtggag | 4080 |
| caggacagca gccaccagac aggaagcacc agcacccaga cacaggagtc caccaatggc | 4140 |
| cagaacagag ggactgagat ccacggtcaa ggcaggagcc agaccagcca ggctgtgaca | 4200 |
| ggaggacaca ctcagataca ggcagggtca cacaccgaga ctgtggagca ggacagaagc | 4260 |
| caaactgtaa gccacggagg ggctagaaa caggacaga cccagacgca gccaggcagt | 4320 |
| ggtcaaagat ggatgcaagt gagcaaccct gaggcaggag agacagtacc gggaggacag | 4380 |
| gcccagactg gggcaagcac tgagtcagga aggcaggagt ggagcagcac tcacccaagg | 4440 |
| cgctgtgtga cagaagggca gggagacaga cagcccacag tggttggtga ggaatgggtt | 4500 |
| gatgaccact caaggagac agtgatcctc aggctggacc agggcaactt gcataccagt | 4560 |
| gtttcctcag cacagggcca ggatgcagcc cagtcagaag agaagcgagg catcacagct | 4620 |
| agagagctgt attcctactt gagaagcacc aagccatgac ttccccgact ccaatgtcca | 4680 |
| gtactggaag aagacagctg gagagagttt ggcttgtcct gcatggccaa tccagtgggt | 4740 |
| gcatccctgg acatcagctc ttcattatgc agcttccctt ttaggtcttt ctcaatgaga | 4800 |
| taatttctgc aaggagcttt ctatcctgaa ctcttctttc ttacctgctt tgcggtgcag | 4860 |
| accctctcag gagcaggaag actcagagca agtcacccct ttgtactgaa ttgtcctcat | 4920 |
| cttgtggggg gtttcaggac tattttatc tctgacatct ctctattgcc ccatctaccc | 4980 |
| taatgcatca ataaaacctt aagccgctgg | 5010 |

<210> SEQ ID NO 3
<211> LENGTH: 1485
<212> TYPE: DNA
<213> ORGANISM: homo sapien

<400> SEQUENCE: 3

| | |
|---|---|
| augccucagu acugcaaaaa cauuaauggg aucaucgagg ccuucaggcg cuaugcaagg | 60 |
| acggagggca cugcacagc gcucacccga ggggagcuga aaagacucuu ggagcaagag | 120 |
| uuugccgaug ugauugugaa accccacgau ccagcaacug uggaugaggu ccugcgucug | 180 |

```
cuggaugaag accacacagg gacuguggaa uucaaggaau uccuggucuu aguguuuaaa    240
guugcccagg ccuguuucaa gacacugagc gagagugcug agggagccug cggcucucaa    300
gagucuggaa gccuccacuc uggggccucg caggagcugg gcgaaggaca gagaaguggc    360
acugaagugg gaagggcggg gaaagggcag cauuaugagg ggagcagcca cagacagagc    420 cagcagggu u ccagagggca gaacaggccu ggguucaga cccagggu ca ggccacuggc     480 ucugcguggg ucagcagcua ugacaggcaa gcugagcccc agagccagga aagaauaagc    540
ccgcagauac aacucucugg gcagacagag cagacccaga aagcuggaga aggcaagagg    600
aaucagacaa cagagaugag gccagagaga cagccacaga ccaggaaaca ggacagagcc    660
caccagacag gugagacugu gacuggaucu ggaacucaga cccaggcagg ugccacccag    720
acuguggagc aggacagcag ccaccagaca ggaagaacca gcaagcagac acaggaggcc    780
accaaugacc agaacagagg gacugagacc cacggucaag gcaggagcca gaccagccag    840
gcugugacag gaggacaugc ucagauacag gcagggacac acaccagac acccacccag    900 accguggagc aggacagcag ccaccagaca ggaagcacca gcacccagac acaggagucc    960
accaauggcc agaacagagg gacugagauc cacggucaag gcaggagcca gaccagccag    1020
gcugugacag gaggacacac ucagauacag gcaggucac acaccgagac uguggagcag   1080
gacagaagcc aaacuguaag ccacggaggg gcuagaaac agggacagac ccagacgcag   1140
ccaggcagug gucaaagaug gaugcaagug agcaacccug aggcaggaga gacaguaccg   1200
ggaggacagg cccagacugg ggcaagcacu gagccaggaa ggcaggagug gagcagcacu   1260
cacccaaggc gcugugugac agaagggcag ggagacagac agcccacagu gguuggugag   1320 gaaugggu ug augaccacuc aagggagaca gugauccuca ggcuggacca gggcaacuug   1380
cauaccagug uuuccucagc acagggccag gaugcagccc agcagaaga gaagcgaggc   1440 aucacagcua gagagcugua uuccuacuug agaagcacca agcca                  1485

<210> SEQ ID NO 4
<211> LENGTH: 237
<212> TYPE: DNA
<213> ORGANISM: homo sapien

<400> SEQUENCE: 4
augccucagu uacugcaaaa cauuaauggg aucaucgagg ccuucaggcg cuaugcaagg     60
acggagggca acugcacagc gcucacccga ggggagcuga aaagacucuu ggagcaagag    120
uuugccgaug ugauugugaa accccacgau ccagcaacug uggaugaggu ccugcgucug    180
cuggaugaag accacacagg gacuugugga auucaaggaa uuccuggucu uagugu u       237

<210> SEQ ID NO 5
<211> LENGTH: 1485
<212> TYPE: DNA
<213> ORGANISM: homo sapien

<400> SEQUENCE: 5
atgcctcagt tactgcaaaa cattaatggg atcatcgagg ccttcaggcg ctatgcaagg     60
acggagggca actgcacagc gctcacccga ggggagctga aaagactctt ggagcaagag    120
tttgccgatg tgattgtgaa accccacgat ccagcaactg tggatgaggt cctgcgtctg    180
ctggatgaag accacacagg gactgtgaa ttcaaggaat tcctggtctt agtgtttaaa     240
gttgcccagg cctgtttcaa gacactgagc gagagtgctg agggagcctg cggctctcaa    300
```

```
gagtctggaa gcctccactc tggggcctcg caggagctgg gcgaaggaca gagaagtggc    360
actgaagtgg gaagggcggg gaaagggcag cattatgagg ggagcagcca cagacagagc    420
cagcagggtt ccagagggca gaacaggcct ggggttcaga cccagggtca ggccactggc    480
tctgcgtggg tcagcagcta tgacaggcaa gctgagtccc agagccagga aagaataagc    540
ccgcagatac aactctctgg gcagacagag cagacccaga aagctggaga aggcaagagg    600
aatcagacaa cagagatgag gccagagaga cagccacaga ccaggaaaca ggacagagcc    660
caccagacag gtgagactgt gactggatct ggaactcaga cccaggcagg tgccacccag    720
actgtggagc aggacagcag ccaccagaca ggaagaacca gcaagcagac acaggaggcc    780
accaatgacc agaacagagg gactgagacc cacggtcaag gcaggagcca gaccagccag    840
gctgtgacag gaggacatgc tcagatacag gcagggacac acaccagac acccacccag    900 accgtggagc aggacagcag ccaccagaca ggaagcacca gcacccagac acaggagtcc    960
accaatggcc agaacagagg gactgagatc cacggtcaag gcaggagcca gaccagccag   1020
gctgtgacag gaggacacac tcagatacag gcagggtcac acaccgagac tgtggagcag   1080
gacagaagcc aaactgtaag ccacggaggg gctagagaac agggacagac ccagacgcag   1140
ccaggcagtg gtcaaagatg gatgcaagtg agcaaccctg aggcaggaga gacagtaccg   1200
ggaggacagg cccagactgg ggcaagcact gagccaggaa ggcaggagtg gagcagcact   1260
cacccaaggc gctgtgtgac agaagggcag ggagacagac agcccacagt ggttggtgag   1320
gaatgggttg atgaccactc aagggagaca gtgatcctca ggctggacca gggcaacttg   1380
cataccagtg tttcctcagc acagggccag gatgcagccc agtcagaaga gaagcgaggc   1440
atcacagcta gagagctgta ttcctacttg agaagcacca agcca                    1485

<210> SEQ ID NO 6
<211> LENGTH: 240
<212> TYPE: DNA
<213> ORGANISM: homo sapien

<400> SEQUENCE: 6
atgcctcagt tactgcaaaa cattaatggg atcatcgagg ccttcaggcg ctatgcaagg     60
acggagggca actgcacagc gctcacccga ggggagctga aaagactctt ggagcaagag    120
tttgccgatg tgattgtgaa accccacgat ccagcaactg tggatgaggt cctgcgtctg    180
ctggatgaag accacacagg gacttgtgga attcaaggaa ttcctggtct tagtgtttaa    240

<210> SEQ ID NO 7
<211> LENGTH: 495
<212> TYPE: PRT
<213> ORGANISM: homo sapien
<220> FEATURE:
<221> NAME/KEY: misc_feature
<222> LOCATION: (27)..(27)
<223> OTHER INFORMATION: Xaa can be Ala or Val
<220> FEATURE:
<221> NAME/KEY: misc_feature
<222> LOCATION: (374)..(374)
<223> OTHER INFORMATION: Xaa can be Gln or His
<220> FEATURE:
<221> NAME/KEY: misc_feature
<222> LOCATION: (480)..(480)
<223> OTHER INFORMATION: Xaa can be Gly or Ser

<400> SEQUENCE: 7

Met Pro Gln Leu Leu Gln Asn Ile Asn Gly Ile Ile Glu Ala Phe Arg
 1               5                  10                  15
```

-continued

```
Arg Tyr Ala Arg Thr Glu Gly Asn Cys Thr Xaa Leu Thr Arg Gly Glu
            20                  25                  30

Leu Lys Arg Leu Leu Glu Gln Glu Phe Ala Asp Val Ile Val Lys Pro
        35                  40                  45

His Asp Pro Ala Thr Val Asp Glu Val Leu Arg Leu Leu Asp Glu Asp
50                      55                  60

His Thr Gly Thr Val Glu Phe Lys Glu Phe Leu Val Leu Val Phe Lys
65                  70                  75                  80

Val Ala Gln Ala Cys Phe Lys Thr Leu Ser Glu Ser Ala Glu Gly Ala
                85                  90                  95

Cys Gly Ser Gln Glu Ser Gly Ser Leu His Ser Gly Ala Ser Gln Glu
            100                 105                 110

Leu Gly Glu Gly Gln Arg Ser Gly Thr Glu Val Gly Arg Ala Gly Lys
        115                 120                 125

Gly Gln His Tyr Glu Gly Ser Ser His Arg Gln Ser Gln Gln Gly Ser
        130                 135                 140

Arg Gly Gln Asn Arg Pro Gly Val Gln Thr Gln Gly Ala Thr Gly
145                 150                 155                 160

Ser Ala Trp Val Ser Ser Tyr Asp Arg Gln Ala Glu Ser Gln Ser Gln
            165                 170                 175

Glu Arg Ile Ser Pro Gln Ile Gln Leu Ser Gly Gln Thr Glu Gln Thr
            180                 185                 190

Gln Lys Ala Gly Glu Gly Lys Arg Asn Gln Thr Thr Glu Met Arg Pro
        195                 200                 205

Glu Arg Gln Pro Gln Thr Arg Glu Gln Asp Arg Ala His Gln Thr Gly
    210                 215                 220

Glu Thr Val Thr Gly Ser Gly Thr Gln Thr Gln Ala Gly Ala Thr Gln
225                 230                 235                 240

Thr Val Glu Gln Asp Ser Ser His Gln Thr Gly Arg Thr Ser Lys Gln
            245                 250                 255

Thr Gln Glu Ala Thr Asn Asp Gln Asn Arg Gly Thr Glu Thr His Gly
        260                 265                 270

Gln Gly Arg Ser Gln Thr Ser Gln Ala Val Thr Gly Gly His Ala Gln
    275                 280                 285

Ile Gln Ala Gly Thr His Thr Gln Thr Pro Thr Gln Thr Val Glu Gln
290                 295                 300

Asp Ser Ser His Gln Thr Gly Ser Thr Ser Thr Gln Thr Gln Glu Ser
305                 310                 315                 320

Thr Asn Gly Gln Asn Arg Gly Thr Glu Ile His Gly Gln Gly Arg Ser
            325                 330                 335

Gln Thr Ser Gln Ala Val Thr Gly Gly His Thr Gln Ile Gln Ala Gly
        340                 345                 350

Ser His Thr Glu Thr Val Glu Gln Asp Arg Ser Gln Thr Val Ser His
    355                 360                 365

Gly Gly Ala Arg Glu Xaa Gly Gln Thr Gln Thr Gln Pro Gly Ser Gly
    370                 375                 380

Gln Arg Trp Met Gln Val Ser Asn Pro Glu Ala Gly Glu Thr Val Pro
385                 390                 395                 400

Gly Gly Gln Ala Gln Thr Gly Ala Ser Thr Glu Ser Gly Arg Gln Glu
                405                 410                 415

Trp Ser Ser Thr His Pro Arg Arg Cys Val Thr Glu Gly Gln Gly Asp
            420                 425                 430

Arg Gln Pro Thr Val Val Gly Glu Glu Trp Val Asp Asp His Ser Arg
```

```
                    435                 440                 445
Glu Thr Val Ile Leu Arg Leu Asp Gln Gly Asn Leu His Thr Ser Val
        450                 455                 460

Ser Ser Ala Gln Gly Gln Asp Ala Ala Gln Ser Glu Lys Arg Xaa
465                 470                 475                 480

Ile Thr Ala Arg Glu Leu Tyr Ser Tyr Leu Arg Ser Thr Lys Pro
                485                 490                 495

<210> SEQ ID NO 8
<211> LENGTH: 79
<212> TYPE: PRT
<213> ORGANISM: homo sapien
<220> FEATURE:
<221> NAME/KEY: misc_feature
<222> LOCATION: (27)..(27)
<223> OTHER INFORMATION: Xaa can be Ala or Val

<400> SEQUENCE: 8

Met Pro Gln Leu Leu Gln Asn Ile Asn Gly Ile Ile Glu Ala Phe Arg
1               5                   10                  15

Arg Tyr Ala Arg Thr Glu Gly Asn Cys Thr Xaa Leu Thr Arg Gly Glu
            20                  25                  30

Leu Lys Arg Leu Leu Glu Gln Glu Phe Ala Asp Val Ile Val Lys Pro
        35                  40                  45

His Asp Pro Ala Thr Val Asp Glu Val Leu Arg Leu Leu Asp Glu Asp
    50                  55                  60

His Thr Gly Thr Cys Gly Ile Gln Gly Ile Pro Gly Leu Ser Val
65                  70                  75

<210> SEQ ID NO 9
<211> LENGTH: 11
<212> TYPE: PRT
<213> ORGANISM: homo sapien

<400> SEQUENCE: 9

Val Glu Phe Lys Glu Phe Leu Val Leu Val Phe
1               5                   10

<210> SEQ ID NO 10
<211> LENGTH: 11
<212> TYPE: PRT
<213> ORGANISM: homo sapien

<400> SEQUENCE: 10

Cys Gly Ile Gln Gly Ile Pro Gly Leu Ser Val
1               5                   10

<210> SEQ ID NO 11
<211> LENGTH: 46
<212> TYPE: DNA
<213> ORGANISM: homo sapien

<400> SEQUENCE: 11
caactttaaa cactaagacc aggaattcct tgaattccac agtccc              46

<210> SEQ ID NO 12
<211> LENGTH: 8
<212> TYPE: PRT
<213> ORGANISM: homo sapien

<400> SEQUENCE: 12

Val Phe Leu Leu Glu Phe Val Gly
```

-continued

```
<210> SEQ ID NO 13
<211> LENGTH: 15
<212> TYPE: PRT
<213> ORGANISM: artificial sequence
<220> FEATURE:
<223> OTHER INFORMATION: Vertebrate 1

<400> SEQUENCE: 13

Val Lys Phe Val Leu Val Leu Phe Glu Lys Phe Glu Val Thr Gly
1               5                   10                  15

<210> SEQ ID NO 14
<211> LENGTH: 15
<212> TYPE: PRT
<213> ORGANISM: artificial sequence
<220> FEATURE:
<223> OTHER INFORMATION: Vertebrate 2

<400> SEQUENCE: 14

Val Lys Phe Val Leu Val Leu Phe Glu Lys Phe Glu Val Thr Gly
1               5                   10                  15

<210> SEQ ID NO 15
<211> LENGTH: 15
<212> TYPE: PRT
<213> ORGANISM: artificial sequence
<220> FEATURE:
<223> OTHER INFORMATION: Vertebrate 3

<400> SEQUENCE: 15

Val Lys Phe Val Leu Val Leu Phe Glu Lys Phe Glu Val Thr Gly
1               5                   10                  15

<210> SEQ ID NO 16
<211> LENGTH: 15
<212> TYPE: PRT
<213> ORGANISM: artificial sequence
<220> FEATURE:
<223> OTHER INFORMATION: Vertebrate 4

<400> SEQUENCE: 16

Val Lys Phe Val Leu Val Leu Phe Glu Lys Phe Glu Val Thr Gly
1               5                   10                  15

<210> SEQ ID NO 17
<211> LENGTH: 15
<212> TYPE: PRT
<213> ORGANISM: artificial sequence
<220> FEATURE:
<223> OTHER INFORMATION: Vertebrate 5

<400> SEQUENCE: 17

Val Lys Phe Val Leu Val Leu Phe Glu Lys Phe Glu Val Thr Gly
1               5                   10                  15

<210> SEQ ID NO 18
<211> LENGTH: 15
<212> TYPE: PRT
<213> ORGANISM: artificial sequence
<220> FEATURE:
<223> OTHER INFORMATION: Vertebrate 6
```

```
<400> SEQUENCE: 18

Val Arg Phe Ile Leu Ser Leu Phe Glu Gly Phe Asp Ile Lys Gly
1               5                   10                  15
```